(12) United States Patent
Belyavsky et al.

(10) Patent No.: US 6,670,123 B1
(45) Date of Patent: Dec. 30, 2003

(54) METHOD FOR DETECTING HEMATOPOIETIC STEM CELLS

(75) Inventors: Alexander Belyavsky, New York, NY (US); Sergey Shmelkov, Union City, NJ (US); Jan Visser, New York, NY (US)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 09/706,594

(22) Filed: Nov. 3, 2000

(51) Int. Cl.[7] ............................. C07H 21/04; C07K 1/00
(52) U.S. Cl. .................... 435/6; 435/2; 435/343; 435/372; 530/350; 530/388.73; 530/827
(58) Field of Search ....................... 435/6, 2, 343, 435/372; 530/350, 388.73, 827

(56) References Cited

U.S. PATENT DOCUMENTS 4,965,204 A * 10/1990 Civin .................... 435/240.27
5,035,994 A * 7/1991 Civin ............................ 435/2
6,242,579 B1 * 6/2001 Lawman et al. ............ 530/935

FOREIGN PATENT DOCUMENTS

EP 1 074 617 A2 2/2001
EP 1074617 * 7/2001 ........... C12N/15/12

OTHER PUBLICATIONS

Nagase et al. Predition of the Coding Sequences of Unidentified Human Genes. XII The Complete Sequences of 100 New cDNA Clones from Brain which Code for Large Proteins in vitro. DNA Research (1998) 5: 355–364.*
O'Hara O., Nagase T. et al., Homo sapiens mRNA for KIAA0918 protein, partial cds. EMBL, European Bioinformatics Institute, AC# AB020725, Feb. 9, 1999.
Ota T. et al., Human cDNA sequence SEQ ID NO: 18664. Geneseq, London: Derwent Publications Ltd. AC# AAH18522, Jun. 26, 2001.
Ota T et al., Human protein sequence SEQ ID NO: 18665, Geneseq, London: Derwent Publications Ltd., AC# AAB95753, Jun. 26, 2001.
Berthou, C. et al., Granzyme B and Perforin Lytic Proteins are Expressed in CD34+ Peripheral Blood Progenitor Cells Mobilized by Chemotherapy and Granulocyte Colony–Stimulating Factor. Blood 86 (9): 3500–3506, 1995.
Ivanova, N.B. et al., Identification of Differentially Expressed Genes by Restriction Endonuclease–Based Gene Expression Fingerprinting. Nucleic Acids Research 23 (15):2954–2958, 1995.
Hatada I. et al., A Genomic Scanning Method for Higher Organisms Using Restriction Sites as Landmarks. Proceedings National Academy of Sciences, USA 88: 9523–9527, 1991.
Uitterlinden, Andre G. et al., Two–dimensional DNA fingerprinting of human individuals. Proceedings National Academy of Sciences, USA, Apr. 1989, vol. 86, pp. 2742–2746.

* cited by examiner

*Primary Examiner*—Long V. Le
*Assistant Examiner*—Changhwa J. Chen
(74) *Attorney, Agent, or Firm*—Amster, Rothstein & Ebenstein LLP

(57) ABSTRACT

The present invention provides an isolated nucleic acid encoding KIAA0918, an isolated nucleic acid that hybridizes under high stringency conditions to a nucleic acid that is complementary to a nucleic acid encoding KIAA0918, a purified KIAA0918 protein, a purified protein encoded by a nucleic acid that hybridizes under high stringency conditions to a nucleic acid that is complementary to a nucleic acid encoding KIAA0918, a method of making KIAA0918 protein, an antibody specific for KIAA0918, a method for producing an antibody specific for KIAA0918 protein, a vector comprising a nucleic acid encoding KIAA0918, and a host cell transformed with a vector comprising a nucleic acid encoding KIAA0918. Also provided are methods for detecting the presence of and isolating hematopoietic stem cells in a heterogeneous cell suspension and for assessing gene expression in a tissue sample.

2 Claims, 5 Drawing Sheets

```
   1 tagacgcgga gcccaaggag gtaaaatgca cacttgctgc cccccagtaa ctttggaaca
  61 ggaccttcac agaaaaatgc atagctggat gctgcagact ctagcgtttg ctgtaacatc
 121 tctcgtcctt tcgtgtgcag aaaccatcga ttattacggg gaaatctgtg acaatgcatg
 181 tccttgtgag gaaaaggacg gcattttaac tgtgagctgt gaaaaccggg ggatcatcag
 241 tctctctgaa attagcccctc cccgtttccc aatctaccac ctcttgttgt ccggaaacct
 301 tttgaaccgt ctctatccca atgagtttgt caattacact ggggcttcaa ttttgcatct
 361 aggtagcaat gttatccagg acattgagac cggggcttttc catgggctac ggggtttgag
 421 gagattgcat ctaaacaata ataaactgga acttctgcga gatgatacct tccttggctt
 481 ggagaacctg gagtacctac aggtcgatta caactacatc agcgtcattg aacccaatgc
 541 ttttgggaaa ctgcatttgt tgcaggtgct tatcctcaat gacaatcttt tgtccagttt
 601 acccaacaat cttttccgtt ttgtgcccttt aacgcacttg gacctccggg ggaaccggct
 661 gaaacttctg ccctacgtgg ggctcttgca gcacatggat aaagttgtgg agctacagct
 721 ggaggaaaac ccttggaatt gttcttgtga gctgatctct ctaaaggatt ggttggacag
 781 catctcctat tcagccctgg tgggggatgt agtttgtgag acccccctcc gcttacacgg
 841 aagggacttg gacgaggtat ccaagcagga acttttgccca aggagactta tttctgacta
 901 cgagatgagg ccgcagacgc ctttgagcac cacgggggtat ttacacacca ccccggcgtc
 961 agtgaattct gtggccactt cttcctctgc tgtttacaaa ccccctttga agccccctaa
1021 ggggactcgc caacccaaca agcccagggt gcgccccacc tctcggcagc cctctaagga
1081 cttgggctac agcaactatg gcccagcat cgcctatcag accaaatccc cggtgccttt
1141 ggagtgtccc accgcgtgct cttgcaacct gcagatctct gatctgggcc tcaacgtaaa
1201 ctgccaggag cgaaagatcg agagcatcgc tgaactgcag cccaagccct acaatcccaa
1261 gaaaatgtat ctgacagaga actacatcgc tgtcgtgcgc aggacagact tcctggaggc
1321 cacggggctg gacctcctgc acctgggggaa taaccgcatc tcgatgatcc aggaccgcgc
1381 tttcggggat ctcaccaacc tgaggcgcct ctacctgaat ggcaacagga tcgagaggct
1441 gagcccggag ttattctatg gcctgcagag cctgcagtat ctcttcctcc agtacaatct
1501 catccgcgag attcagtctg gaacttttga cccggtccca aacctccagc tgctattctt
1561 gaataacaac ctcctgcagg ccatgccctc aggcgtcttc tctggcttga ccctcctcag
1621 gctaaacctg aggagtaaac acttcacctc cttgccagtg agtggagttt tggaccagct
1681 gaagtcactc atccaaatcg acctgcatga caatccttgg gattgtacct gtgacattgt
1741 gggcatgaag ctgtgggtgg agcagctcaa agtgggcgtc ctagtggacg aggtgatctg
1801 taaggcgccc aaaaaattcg ctgagaccga catgcgctct attaagtcgg agctgctgtg
1861 ccctgactat tcagatgtag tagtttccac gcccacaccc tcctctatcc aggtccctgc
1921 gaggaccagc gccgtgactc ctgcggtccg gttgaatagc accggggccc ccgcgagctt
1981 gggcgcaggc ggaggggcgt cgtcggtgcc cttgtctgtg ttaattctca gcctcctgct
2041 ggttttcatc atgtccgtct tcgtggccgc cgggctcttc gtgctggtca tgaagcgcag
2101 gaagaagaac cagagcgacc acaccagcac caacaactcc gacgtgagct cctttaacat
2161 gcagtacagc gtgtacggcg gcggcggcgg cacgggcggc cacccacacg cgcacgtgca
2221 tcaccgcggg cccgcgctgc ccaaggtgaa gacgcccgcg ggcacgtgt atgaatacat
2281 cccccaccca ctgggccaca tgtgcaaaaa ccccatctac cgctcccgag agggcaactc
2341 cgtagaggat tacaaagacc tgcacgagct caaggtcacc tacagcagca accaccacct
2401 gcagcagcag cagcagccgc cgccgccacc gcagcagcca cagcagcagc ccccgccgca
2461 gctgcagctg cagcctgggg aggaggagag gcgggaaagc caccacttgc ggagccccgc
2521 ctacagcgtc agcaccatcg agccccggga ggacctgctg tcgccggtgc aggacgccga
2581 ccgcttttac agggcattt tagaaccaga caaacactgc tccaccacce ccgccggcaa
2641 tagcctcccg gaatatccca aattcccgtc cagcccccgct gcttacactt tctccccccaa
2701 ctatgacctg agacgccccc atcagtattt gcaccccgggg gcaggggaca gcaggctacg
2761 ggaaccggtg ctctacagcc cccgagtgc tgtctttgta gaacccaacc ggaacgaata
2821 tctggagtta aaaagcaaaac taaacgttga gccggactac ctcgaagtgc tggaaaaaca
2881 gaccacgttt agccagttct aaaagcaaag aaactctctt ggagcttttg catttaaaac
2941 aaacaagcaa gcagacacac acagtgaaca catttgatta attgtgttgt ttcaacgttt
3001 aggggtgaagt gccttggcac gggatttctc agcttcggtg gaagatacga aaagggtgtg
3061 caatttcctt taaaatttac acgtgggaaa catttgtgta aactgggcac atcactttct
3121 cttcttgcgt gtgggggcagg tgtggagaag ggcttttaagg aggccaattt gctgcgcggg
3181 tgacctgtga aaggtcacag tcattttttgt agtggttgga agtgctaaga atggtggatg
3241 atggcagage atagattcta ctcttcctct tttgcttcct cccccctccc cgccccctgcc
3301 ccacctctct ttctcccctt taagccatg ggtgggtcta actggcttt gtggagaaat
3361 tagcacaccc caacttaat aggaaatttg ttctcttttt ccgcccctct ccttctctcc
3421 tcccctccccc tcccttctca ttccttttct ttgttttaa aggatgtgtt tgtatgcatt
3481 ctggacattt gaattaaaaa aaaagtattg tgatcctgta aaggatcacc atagatgtgg
3541 acaaatcatt aaaattacag agctatatga tccataattg attagtcaaa ataacttatt
3601 gatgaaatat acaaatattt tattgtagca cctatttta tatgcacatt tagcattcct
3661 ctttccttca ctatttagcc tatgatttg cagaggtgtc acactgtatt aggatctgca
3721 tttctaaaac tgacgtggta tcaggaaggc attttcaatc attcaaaatg tggagaattt
3781 aatggctaaa tcttttaaaag ccaatgcaac ccacccaatt gaatctgcat tttctttttaa
3841 gaaaacagag ctgattgtat cccaatgtat tttaaaaat aggggcaattg attgggccat
3901 tccgagagaa ttgttttgcaa gtttttgggtt ttattagaaa atatttgaaa gtatttttat
3961 taatgaacca aaatgcacatg ttcatttgac tactattgta gccgtatttc gattgtttaa
4021 ccaaacccag ttgcatttgt acagatccac gtgtactggc acctcagaag accaaatcat
4081 ggactgtaca agtctctata caatgtctttt atccctgtgg gcagcaagca atgatgataa
4141 tgacaaacag gatatctgta agatggggct actgttgtta cagtctcata tgtatcccag
4201 cacatgtaat tttttaaata gtttctgaat aaacacttga taactatgtc
```

Fig. 4

MHTCCPPVTLEQDLHRKMHSWMLQTLAFAVTSLVLS
CAETIDYYGEICDNACPCEEKDGILTVSCENRGIISLSEISPPRFPIYHLLLSGNLLN
RLYPNEFVNYTGASILHLGSNVIQDIETGAFHGLRGLRRLHLNNNKLELLRDDTFLGL
ENLEYLQVDYNYISVIEPNAFGKLHLLQVLILNDNLLSSLPNNLFRFVPLTHLDLRGN
RLKLLPYVGLLQHMDKVVELQLEENPWNCSCELISLKDWLDSISYSALVGDVVCETPF
RLHGRDLDEVSKQELCPRRLISDYEMRPQTPLSTTGYLHTTPASVNSVATSSSAVYKP
PLKPPKGTRQPNKPRVRPTSRQPSKDLGYSNYGPSIAYQTKSPVPLECPTACSCNLQI
SDLGLNVNCQERKIESIAELQPKPYNPKKMYLTENYIAVVRRTDFLEATGLDLLHLGN
NRISMIQDRAFGDLTNLRRLYLNGNRIERLSPELFYGLQSLQYLFLQYNLIREIQSGT
FDPVPNLQLLFLNNNLLQAMPSGVFSGLTLLRLNLRSNHFTSLPVSGVLDQLKSLIQI
DLHDNPWDCTCDIVGMKLWVEQLKVGVLVDEVICKAPKKFAETDMRSIKSELLCPDYS
DVVVSTPTPSSIQVPARTSAVTPAVRLNSTGAPASLGAGGGASSVPLSVLILSLLLVF
IMSVFVAAGLFVLVMKRRKKNQSDHTSTNNSDVSSFNMQYSVYGGGGGTGGHPHAHVH
HRGPALPKVKTPAGHVYEYIPHPLGHMCKNPIYRSREGNSVEDYKDLHELKVTYSSNH
HLQQQQQPPPPPQQPQQQPPPQLQLQPGEEERRESHHLRSPAYSVSTIEPREDLLSPV
QDADRFYRGILEPDKHCSTTPAGNSLPEYPKFPCSPAAYTFSPNYDLRRPHQYLHPGA
GDSRLREPVLYSPPSAVFVEPNRNEYLELKAKLNVEPDYLEVLEKQTTFSQF

Fig. 5

METHOD FOR DETECTING HEMATOPOIETIC STEM CELLS

BACKGROUND OF THE INVENTION

In vertebrates, most tissues are composed of differentiated cells that no longer divide. Nevertheless, there are tissues which retain an 'embryonic' cell population within themselves. The cellular composition of such embryonic populations is always changing, even in adult animals. This phenomenon is most evident in the mammalian hematopoietic system. This system, which is organized hierarchically, consists of a heterogeneous mixture of many different kinds of blood cells at all stages of differentiation—some morphologically recognizable and some not [23]. Mature, functional blood cells are divided into several lines, including erythroid, lymphoid, and myeloid, each possessing its own morphology, characteristics, and function. Each blood line derives from restricted progenitor cells, which become committed to a particular line of differentiation. However, despite this diversity, the various developing blood cells and progenitor cells derive from one discreet source: the embryonic cell population of multipotential, self-renewing hematopoietic stem cells [21, 22].

A stem cell is a cell capable of extensive proliferation: it generates more stem cells (through self-renewal) in addition to its differentiated progeny [20, 21]. In mammals and birds, a multipotential hematopoietic stem cell can give rise to red blood cells (erythrocytes), white blood cells (granulocytes), macrophages, platelets, and immunocompetent cells (lymphocytes) [22]. Thus, a single hematopoietic stem cell can generate a clone containing millions of differentiated cells, as well as a few stem cells. The continuous formation of new blood cells is accomplished in bone marrow by hematopoietic stem cells. Stem cells mature into progenitor cells, which then become lineage-committed, although not yet terminally-differentiated. Once committed, progenitor cells are no longer capable of maturing into all of the cell lineages which comprise the hematopoietic system [22].

Hematopoietic stem cells currently find use in a myriad of clinical settings. Indeed, with the recent remarkable progress in cell processing technology, there has been a rapid increase in the number of patients and types of diseases that are now treated with hematopoietic stem-cell transplantation, in both autologous and allogeneic cases. For example, autologous peripheral stem-cell support has largely replaced bone marrow transplantation as a means of regenerating the hematopoietic system of myeloma patients undergoing myeloablative chemotherapy. Stem cell transplantation is also used to treat patients with non-Hodgkin's lymphomas [25]. Moreover, peripheral blood autografting has been widely used in trials for the treatment of chemosensitive tumors [26].

Hematopoietic stem cells also may be used in vitro to enable the detection and assessment of growth factors associated with stem cell self-renewal and hematopoietic development. Furthermore, in vitro expansion of hematopoietic stem cells from various sources, including bone marrow and blood of the umbilical cord, is gaining importance, as it provides a clinically-potential graft in autologous or allogeneic transplant cases, and facilitates transduction of genes for the treatment of genetic diseases through gene therapy [24].

To be useful, however, hematopoietic stem cells first must be identified and isolated—a task made more difficult by the fact that hematopoietic stem cells comprise only a small proportion of the total cell population in bone marrow. Hematopoietic stem cells may be identified, for example, by detecting expression of specific cell-surface protein or carbohydrate antigen markers.

The CD34 antigen, which is a glycosylated transmembrane protein, has frequently been used as a marker for the identification of hematopoietic stem cells [26]. Detection of CD34 is also considered by some to be the first step in quality assessment of hematopoietic stem cell grafts [27]. The CD34 antigen was previously indicated to be present solely on stem cells, and not on lineage-committed progenitor cells. However, recent evidence suggests that expression of CD34 on the cell membrane does not always correlate with stem cell activity [28]. Indeed, in the mouse, there is a highly quiescent population of stem cells that lacks CD34 expression, but which has full reconstituting capacity. It also has been discovered that there is a similar population of dormant CD34-negative human hematopoietic stem cells. This information clearly casts some uncertainty on the benefits of using CD34 as a marker for isolating hematopoietic stem cells [28].

While it appears that lineage-committed hematopoietic cells may display epitopic characteristics associated with hematopoietic stem cells, it is not known how many of the antigen markers associated with differentiated cells are also present on stem cells. Accordingly, it is clear that significant problems exist in connection with the identification of hematopoietic stem cells, and new methods of detection of hematopoietic stem cells are needed.

SUMMARY OF THE INVENTION

The present invention is predicated on the discovery that the KIAA0918 gene is specifically expressed in the primitive hematopoietic Kg-1a cell line, which is close to the hematopoietic stem cell line, thereby providing a genetic marker for identifying hematopoietic stem cells. On the basis of this finding, the present invention provides an isolated nucleic acid sequence encoding KIAA0918, and an isolated nucleic acid sequence that hybridizes under high stringency conditions to a second nucleic acid that is complementary to a nucleic acid sequence encoding KIAA0918.

The present invention also discloses a purified KIAA0918 protein, and a purified protein encoded by a nucleic acid sequence that hybridizes under high stringency conditions to a second nucleic acid sequence that is complementary to a nucleic acid sequence encoding KIAA0918. Also provided is a method of making KIAA0918 protein.

The present invention is further directed to an antibody specific for KIAA0918, and a method for producing an antibody specific for KIAA0918 protein.

Additionally, the present invention discloses a vector comprising a nucleic acid sequence encoding KIAA0918, and a host cell transformed with a vector comprising a nucleic acid sequence encoding KIAA0918.

Also provided in the present invention is a method for detecting the presence of hematopoietic stem cells in a heterogeneous cell suspension that may contain hematopoietic stem cells, as well as a method for isolating hematopoietic stem cells from a heterogeneous cell suspension that may contain hematopoietic stem cells.

Finally, the present invention discloses a method for assessing gene expression in a tissue sample.

Additional objects of the present invention will be apparent in view of the description which follows.

BRIEF DESCRIPTION OF THE FIGURES

FIG. 4 depicts the nucleotide sequence of human KIAA0918 (SEQ ID NO:6).

FIG. 5 depicts the amino acid sequence of human KIAA0918 (SEQ ID NO:5).

DETAILED DESCRIPTION OF THE INVENTION

Figure 1:
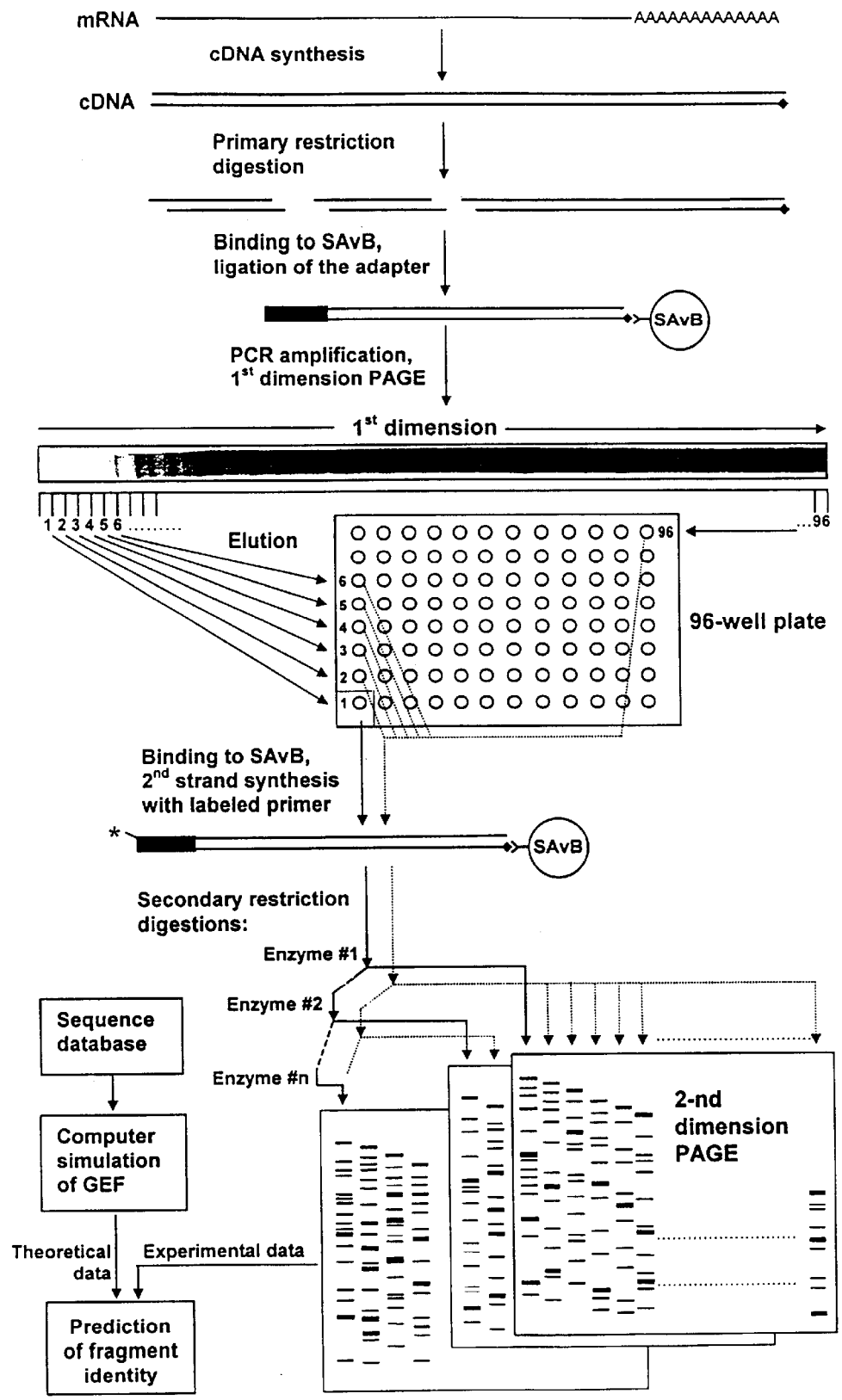
FIG. 1 depicts a scheme of the two-dimensional gene expression fingerprinting procedure and the computer-assisted prediction of cDNA fragment identity. The first dimension strip in the middle of the figure corresponds to the cDNA sample obtained from Kg-1 cells using NdeII as primary enzyme. ♦=biotin groups; SavB=Streptavidin beads

The present invention provides an isolated nucleic acid sequence encoding KIAA0918. KIAA0918 is a protein which has previously been identified, but for which there was previously no known use. As used herein, KIAA0918 includes, where appropriate, both a KIAA0918 protein and a "KIAA0918 analogue". Unless otherwise indicated, "protein" shall mean a protein, protein domain, polypeptide, or peptide. A "KIAA0918 analogue" may be any protein having functional similarity to the KIAA0918 protein that is 80% or greater (preferably, 90% or greater) in amino-acid-sequence homology with the KIAA0918 protein.

The nucleic acid sequence of the present invention may be genomic DNA, cDNA, RNA, or antisense RNA, and may be derived from any species. The nucleic sequence of the present invention is preferably derived from a mammalian species, and, more preferably, from a human. The nucleic acid sequence of the present invention preferably comprises the nucleotide sequence of FIG. 4 (including conservative substitutions thereof). "Conservative substitutions" are those amino acid substitutions which are functionally equivalent to the substituted amino acid residue, either because they have similar polarity or steric arrangement, or because they belong to the same class as the substituted residue (e.g., hydrophobic, acidic, or basic). The nucleic acid of the present invention also may encode a KIAA0918 protein comprising the amino acid sequence set forth in FIG. 5.

The present invention further discloses an isolated nucleic acid sequence that hybridizes under high stringency conditions (e.g., hybridization to filter-bound DNA in 0.5-M NaHPO$_4$ at 65° C. and washing in 0.1×SSC/0.1% SDS at 68° C.) or moderate stringency conditions (e.g., washing in 0.2×SSC/0.1% SDS at 42° C.) [29] to a second nucleic acid that is complementary to the nucleotide sequence set forth in FIG. 4 or a contiguous fragment thereof. In addition, the present invention provides a nucleic acid sequence encoding KIAA0918 protein having one or more mutations that result in the expression of either a non-functional or mutant protein, or in a lack of expression altogether. The mutation may be generated by at least one point, insertion, rearrangement, or deletion mutation, or a combination thereof.

The present invention also provides an isolated and purified KIAA0918 protein. The KIAA0918 protein may be isolated from tissue obtained from a subject, or recombinantly produced as described below. The KIAA0918 protein of the present invention may comprise the amino acid sequence set forth in FIG. 5. Alternatively, the KIAA0918 protein of the present invention may be encoded by the nucleotide sequence set forth in FIG. 4.

The present invention is further directed to a purified protein encoded by a nucleic acid sequence that hybridizes under high stringency or moderate stringency conditions to a second nucleic acid sequence that is complementary to the nucleotide sequence set forth in FIG. 4 or a contiguous fragment thereof.

The present invention also provides agents that bind to KIAA0918 protein. The agent may include, without limitation, an antibody, a compound, a drug, a Fab fragment, a F(ab')$_2$ fragment, a molecule, a nucleic acid, a protein (including a growth factor), a polypeptide, a peptide, a nucleic acid (including DNA, RNA, mRNA, antisense RNA), and any combinations thereof. Moreover, an agent that binds to KIAA0918 protein may be either natural or synthetic. A Fab fragment is a univalent antigen-binding fragment of an antibody, which is produced by papain digestion. An F(ab')$_2$ fragment is a divalent antigen-binding fragment of an antibody, which is produced by pepsin digestion. Agents that bind to KIAA0918 protein may be identified or screened by contacting the protein with the agent of interest, and assessing the ability of the agent to bind to the protein.

The agent of the present invention is preferably an antibody specific for, or immunoreactive with, KIAA0918. The antibody of the present invention may be monoclonal or polyclonal. Furthermore, the antibody of the present invention may be produced by techniques well known to those skilled in the art. The antibody of the present invention may be incorporated into kits which include an appropriate labeling system, buffers, and other necessary reagents for use in a variety of detection and diagnostic applications. Labeling of the antibody of the present invention may be accomplished by standard techniques using one of the variety of different chemiluminescent and radioactive labels known in the art.

The present invention further provides a method for producing an antibody specific for KIAA0918 protein, comprising the steps of: (a) immunizing a mammal with KIAA0918 protein; and (b) purifying antibody from a tissue of the mammal or from a hybridoma made using tissue of the mammal. For example, a polyclonal antibody may be produced by immunizing a rabbit, mouse, or rat with purified KIAA0918. Thereafter, a monoclonal antibody may be produced by removing the spleen from the immunized rabbit, mouse, or rat, and fusing the spleen cells with myeloma cells to form a hybridoma which, when grown in culture, will produce a monoclonal antibody. Also provided is an antibody produced by this method.

The present invention further discloses agents that bind to a nucleic acid encoding KIAA0918 protein. Suitable agents include, but are not limited to, a an antibody, a compound, a drug, a Fab fragment, a F(ab')$_2$ fragment, a molecule, a nucleic acid, a protein, a polypeptide, a peptide, a nucleic acid (including DNA, RNA, mRNA, antisense RNA), and any combinations thereof. The agents that bind to a nucleic acid encoding KIAA0918 may inhibit or promote expression of the nucleic acid. Such agents may be discovered by a method for screening for an agent that binds to a nucleic acid encoding KIAA0918, comprising contacting the nucleic acid with an agent of interest, and assessing the ability of the agent to bind to the nucleic acid. An agent that inhibits or promotes the expression of a nucleic acid encoding KIAA0918 may be screened by contacting a host cell transformed with a vector comprising the nucleic acid, and assessing the agent's effect on expression of the nucleic acid.

The present invention also provides nucleic acid probes and mixtures thereof which hybridize to nucleic acid encoding KIAA0918 protein. Such probes may be prepared by a variety of techniques known to those skilled in the art, including, without limitation, PCR and restriction-enzyme digestion of nucleic acid encoding KIAA0918; and automated synthesis of oligonucleotides whose sequences correspond to selected portions of the nucleotide sequence of nucleic acid encoding KIAA0918, using commercially-available oligonucleotide synthesizers such as the Applied Biosystems Model 392 DNA/RNA synthesizer. The nucleic acid probes of the present invention also may be prepared so that they contain at least one point, insertion, rearrangement, or deletion mutation, or a combination thereof, to correspond to mutations of the KIAA0918 gene.

The nucleic acid probes of the present invention may be DNA or RNA, and may vary in length from about 8 nucleotides to the entire length of the nucleic acid encoding KIAA0918. Preferably, the probes are 8 to 30 nucleotides in length. Labeling of the nucleic acid probes may be accomplished using one of a number of methods known in the art, including, without limitation, PCR, nick translation, end labeling, fill-in end labeling, polynucleotide kinase exchange reaction, random priming, or SP6 polymerase (for riboprobe preparation), and one of a variety of labels, including, without limitation, radioactive labels such as $^{35}S$, $^{32}P$, or $^{3}H$ and nonradioactive labels such as biotin, fluorescein (FITC), acridine, cholesterol, or carboxy-X-rhodamine (ROX). Combinations of two or more nucleic probes, corresponding to different or overlapping regions of nucleic acid encoding KIAA0918, also may be included in kits for use in a variety of detection and diagnostic applications.

The present invention is further directed to a vector comprising a nucleic acid sequence encoding KIAA0918 protein. The vector of the present invention may comprise the nucleotide sequence of FIG. 4 or a contiguous fragment thereof. Alternatively, the vector of the present invention may comprise a nucleic acid sequence which hybridizes under high stringency or moderate stringency conditions to a nucleic acid sequence that is complementary to the nucleotide sequence set forth in FIG. 4, or to a contiguous fragment thereof.

The vector of the present invention may be constructed by inserting nucleic acid encoding KIAA0918 into a suitable vector nucleic acid operably linked to an expression control sequence, as described below. The term "inserted", as used herein, means the ligation of a foreign DNA fragment with vector DNA, by techniques such as the annealing of compatible cohesive ends generated by restriction endonuclease digestion, or by the use of blunt-end ligation techniques. Other methods of ligating DNA molecules will be apparent to one skilled in the art.

The vector of the present invention may be derived from a number of different sources, including plasmids, viral-derived nucleic acids, lytic bacteriophage derived from phage lambda, cosmids, or filamentous single-stranded bacteriophages such as M13. Depending upon the type of host cell into which the vector is introduced, vectors may be bacterial or eukaryotic. Bacterial vectors are derived from many sources, including the genomes of plasmids and phages. Eukaryotic vectors are constructed from a number of different sources, e.g., yeast plasmids and viruses. Some vectors, referred to as shuttle vectors, are capable of replicating in both bacteria and eukaryotes. The nucleic acid from which the vector is derived is usually greatly reduced in size, such that only those genes essential for its autonomous replication remain. This reduction in size enables the vectors to accommodate large segments of foreign DNA. Examples of suitable vectors into which nucleic acid encoding KIAA0918 can be inserted include, but are not limited to, pCGS, pBR322, pUC18, pUC19, pHSV-106, pJS97, pJS98, M13mp18, M13mp19, pSPORT 1, pGem, pSPORT 2, pSV●SPORT 1, pBluescript II, λZapII, λgt10, λgt11, λgt22A, and λZIPLOX. Other suitable vectors will be obvious to one skilled in the art.

The vector of the present invention may be introduced into a host cell. Accordingly, the present invention provides a host cell transformed with the vector of the present invention. The term "host cell", as used herein, means the bacterial or eukaryotic cell into which the vector is introduced. The term "transform" denotes the introduction of a vector into a bacterial or eukaryotic host cell. Additionally, as used herein, the term "introduction" is a general term indicating that one of a variety of means has been used to allow the vector to enter the intracellular environment of the host cell in such a way that the nucleic acid exists in stable form, and may be expressed, therein. As such, it encompasses transformation of bacterial cells, as well as transfection, transduction, and related methods in eukaryotic cells. The vector of the present invention may exist in integrated or unintegrated form within the host cell. When in unintegrated form, the vector is capable of autonomous replication.

Any one of a number of suitable bacterial or eukaryotic host cells may be transformed with the vector of the present invention. Examples of suitable host cells are known to one skilled in the art, and include, without limitation, bacterial cells such as *Escherichia coli* strains c600, c600hfl, HB101, LE392, Y1090, JM103, JM109, JM101, JM107, Y1088, Y1089, Y1090, Y1090(ZZ), DM1, PH10B, DH11S, DH125, RR1, TB1 and SURE, *Bacillus subtilis, Agrobacterium tumefaciens, Bacillus megaterium;* and eukaryotic cells such as *Pichia pastoris, Chlamydomonas reinhardtii, Cryptococcus neoformans, Neurospora crassa, Podospora anserina, Saccharomyces cerevisiae, Saccharomyces pombe, Uncinula necator*, cultured insect cells, cultured chicken fibroblasts, cultured hamster cells, cultured human cells such as HT1080, MCF7, and 143B, and cultured mouse cells such as EL4 and NIH3T3 cells.

Some bacterial and eukaryotic vectors have been engineered so that they are capable of expressing inserted nucleic acids to high levels within the host cell. An "expression cassette" or "expression control sequence", comprising nucleic acid encoding a KIAA0918 protein operably linked or under the control of transcriptional and translational regulatory elements (e.g., a promoter, ribosome binding site, operator, or enhancer), can be made and used for expression of KIAA0918 protein in vitro or in vivo. As used herein, "expression" refers to the ability of the vector to transcribe the inserted nucleic acid into mRNA, so that synthesis of the protein encoded by the inserted nucleic acid can occur. The choice of regulatory elements employed may vary, depending on such factors as the host cell to be transformed and the desired level of expression.

For example, in vectors used for the expression of a gene in a bacterial host cell such as *Escherichia coli*, the lac operator-promoter or the tac promoter is often used. Eukaryotic vectors use promoter-enhancer sequences of viral genes, especially those of tumor viruses. Several promoters for use in mammalian cells are known in the art and include, for example, the phosphoglycerate (PGK) promoter, the simian virus 40 (SV40) early promoter, the Rous sarcoma virus (RSV) promoter, the adenovirus major late promoter (MLP), and the human cytomegalovirus (CMV) immediate early 1 promoter. However, any promoter that facilitates suitable expression levels can be used in the present invention. Inducible promoters (e.g., those obtained from the heat shock gene, metallothionine gene, beta-interferon gene, or steroid hormone responsive genes, including, without limitation, the lac operator-promoter in *E. coli* and metallothionine or mouse mammary tumor virus promoters in eukaryotic cells) may be useful for regulating transcription based on external stimuli.

Vectors suitable for expression in a host cell of nucleic acid encoding KIAA0918 are well-known to one skilled in the art, and include pET-3d (Novagen), pProEx-1 (Life Technologies), pFastBac 1 (Life Technologies), pSFV (Life Technologies), pcDNA II (Invitrogen), pSL301 (Invitrogen), pSE280 (Invitrogen), pSE380 (Invitrogen), pSE420 (Invitrogen), pTrcHis A,B,C (Invitrogen), pRSET A,B,C (Invitrogen), pYES2 (Invitrogen), pAC360 (Invitrogen), pVL1392 and pVl1392 (Invitrogen), pCDM8 (Invitrogen), pcDNA I (Invitrogen), pcDNA I(amp) (Invitrogen), pZeoSV (Invitrogen), pcDNA 3 (Invitrogen), pRc/CMV (Invitrogen), pRc/RSV (Invitrogen), pREP4 (Invitrogen), pREP7 (Invitrogen), pREP8 (Invitrogen), pREP9 (Invitrogen), pREP10 (Invitrogen), pCEP4 (Invitrogen), pEBVHis (Invitrogen), and λPop6. Other vectors will be apparent to one skilled in the art.

The vector of the present invention may be introduced into a host cell using conventional procedures known in the art, including, without limitation, electroporation, DEAE Dextran transfection, calcium phosphate transfection, mono-cationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. For the purposes of gene transfer into a host cell, tissue, or subject, a recombinant vector containing nucleic acid encoding KIAA0918 may be combined with a sterile aqueous solution which is preferably isotonic with the blood of the recipient. Such formulations may be prepared by suspending the recombinant vector in water containing physiologically-compatible substances, such as sodium chloride, glycine, and the like, and having buffered pH compatible with physiological conditions, to produce an aqueous solution, then rendering the solution sterile. In a preferred embodiment of the invention, the recombinant vector is combined with a 20–25% sucrose in saline solution in preparation for introduction into a mammal.

The present invention further provides a method of making recombinant KIAA0918 protein, comprising the steps of: (a) introducing into a suitable bacterial or eukaryotic host cell a nucleic acid sequence encoding KIAA0918 (or a nucleic acid that hybridizes under high stringency conditions or moderate stringency conditions to a second nucleic acid that is complementary to the nucleotide sequence set forth in FIG. 4 or a contiguous fragment thereof); (b) maintaining the host cell under conditions such that the nucleic acid sequence is expressed to produce KIAA0918 protein; and (c) recovering the recombinant KIAA0918 protein from the culture medium, from the host cells, or from cell lysate. As used herein, the term "recombinant" refers to KIAA0918 produced by purification from a host cell transformed with a vector capable of directing its expression to a high level. In the method of the present invention, a nucleic acid sequence encoding KIAA0918 may be introduced into a suitable host cell by any of the above-described methods.

A variety of methods of growing host cells transformed with a vector are known to those skilled in the art. The type of host cell (i.e., bacterial or eukaryotic) is the primary determinant of both the method to be utilized and the optimization of specific parameters relating to such factors as temperature, trace nutrients, humidity, and growth time. Depending on the vector used, the host cells may have to be induced by the addition of a specific compound at a certain point in the growth cycle, in order to initiate expression of the nucleic acid contained in the vector. Examples of compounds used to induce expression of the nucleic acid contained in the vector are known to one skilled in the art, and include, without limitation, IPTG, zinc, and dexamethasone. Using standard methods of protein isolation and purification, such as ammonium sulfate precipitation and subsequent dialysis to remove salt, followed by fractionation according to size, charge of the protein at specific pH values, affinity methods, etc., recombinant KIAA0918 may be extracted from suitable host cells transformed with a vector capable of expressing nucleic acid encoding KIAA0918.

The present invention also discloses a method for detecting the presence of hematopoietic stem cells in a heterogeneous cell suspension that may contain hematopoietic stem cells. The heterogeneous cell suspension may be, for example, adult bone marrow, embryonic yolk sac, fetal liver, adult peripheral blood, spleen, or umbilical cord blood. Moreover, the heterogeneous cell suspension may be a tissue sample obtained from any mammal (e.g., humans, domestic animals, and commercial animals), but is preferably obtained from a human. A sample of cells from a mammal may be removed using standard procedures, including biopsy and aspiration.

The method of the present invention comprises detecting cells expressing KIAA0918 in a heterogeneous cell suspension, wherein the detection of expression of KIAA0918 indicates the presence of hematopoietic stem cells. Expression of KIAA0918 may be detected using an agent reactive with KIAA0918. As used herein, "reactive" means the agent has affinity for, binds to, or is directed against KIAA0918. The agent may be an antibody, a compound, a drug, a Fab fragment, a F(ab')$_2$ fragment, a molecule, a nucleic acid, a protein (including a growth factor), a polypeptide, a peptide, a nucleic acid (including DNA, RNA, mRNA, antisense RNA), and any combinations thereof. Furthermore, the agent may be labeled with a detectable marker.

For example, the agent of the present invention may be a monoclonal or polyclonal antibody. Preferably, the antibody is a high-affinity antibody, labeled with a detectable marker. The antibody of the present invention may be produced by techniques well known to those skilled in the art, including those described above, and may be labeled with detectable markers, in accordance with the above-described methods. Where the agent is an antibody immunoreactive with KIAA0918, expression of KIAA0918 may be detected from standard immunological detection techniques. For example, the method may be performed by contacting the heterogeneous cell suspension with an antibody immunoreactive with KIAA0918, under conditions permitting the antibody to bind to KIAA0918, if present in the suspension, to form an antibody-KIAA0918 complex. Appropriate binding conditions (e.g., temperature, pH, and salt concentration) are readily determinable by the skilled artisan. Thereafter, the presence of the complex may be detected by a variety of immunological detection techniques, including an ELISA assay, a Western blot, flow cytometry, hemagglutination, or any other immunostaining method employing an antigen-antibody interaction.

Alternatively, the agent of the present invention may be a nucleic acid probe which hybridizes to nucleic acid encoding KIAA0918. The presence of cells expressing KIAA0918 in a heterogeneous cell suspension may be detected using hybridization analysis of nucleic acid extracted from the heterogeneous cell suspension. According to this method of the present invention, the hybridization analysis may be conducted using one or more nucleic acid probes which hybridize to nucleic acid encoding KIAA0918. The probes may be prepared by a variety of techniques known to those skilled in the art, including, without limitation, restriction enzyme digestion of nucleic acid encoding KIAA0918; and automated synthesis of oligonucleotides whose sequences correspond to selected portions of the nucleotide sequence of nucleic acid encoding KIAA0918, using commercially-available oligonucleotide synthesizers, such as the Applied Biosystems Model 392 DNA/RNA synthesizer.

The nucleic acid probes used in the present invention may be DNA or RNA, and may vary in length from about 8 nucleotides to the entire length of the nucleic acid encoding KIAA0918. The nucleic acid used in the probes may be derived from mammalian KIAA0918. The nucleotide sequence for human KIAA0918 is depicted in FIG. 4. Using this sequence as a probe, the skilled artisan could readily clone corresponding KIAA0918 cDNA from other species. In addition, the nucleic acid probes of the present invention may be labeled with one or more detectable markers. Labeling of the nucleic acid probes may be accomplished using one of a number of methods known in the art (e.g., nick translation, end labeling, fill-in end labeling, polynucleotide kinase exchange reaction, random priming, or SP6 polymerase for riboprobe preparation), along with one of a variety of labels (e.g., radioactive labels, such as $^{35}S, ^{32}P$, or $^{3}H$, or nonradioactive labels, such as biotin, fluorescein (FITC), acridine, cholesterol, or carboxy-X-rhodamine (ROX)). Combinations of two or more nucleic acid probes (or primers), corresponding to different or overlapping regions of the nucleic acid encoding KIAA0918, also may be used to detect expression of KIAA0918, using, for example, PCR or RT-PCR.

The present invention also contemplates the provision of a kit for performing a method of detecting the presence of hematopoietic stem cells in a heterogeneous cell suspension that may contain hematopoietic stem cells, as described above. The kit would include a container, an agent which binds to KIAA0918 to form a complex, and a reagent or reagents capable of detecting the resulting complex. As noted above, the agent may be any of an antibody, a compound, a drug, a Fab fragment, a F(ab')$_2$ fragment, a molecule, a nucleic acid, a protein (including a growth factor), a polypeptide, a peptide, a nucleic acid (including DNA, RNA, mRNA, antisense RNA), and any combinations thereof. The reagent or reagents capable of detecting the complex are preferably secondary antibodies that bind selectively to one or the other of the antibody and KIAA0918, preferably KIAA0918, and which are further linked, either through a covalent linkage or by a noncovalent linkage, to a reporter molecule, including, without limitation, an enzyme, a fluorescent molecule, a light-emitting molecule, or a radioactive molecule. If antibody binding to hematopoietic stems cells results in cell agglutination, the reagent capable of detecting the resulting complex will not be necessary.

The present invention is also directed to a method for isolating hematopoietic stem cells from a heterogeneous cell suspension that may contain hematopoietic stem cells. The heterogeneous cell suspension may be, for example, adult bone marrow, embryonic yolk sac, fetal liver, adult peripheral blood, spleen, and umbilical cord blood. Moreover, the heterogeneous cell suspension may be a tissue sample obtained from any mammal (e.g., humans, domestic animals, and commercial animals), but is preferably obtained from a human. A sample of cells from a mammal may be removed using standard procedures, including biopsy and aspiration.

The method of the present invention comprises contacting the heterogeneous cell suspension with a monoclonal antibody specific for KIAA0918, and separating from the heterogeneous cell suspension cells to which the monoclonal antibody is bound. A monoclonal antibody specific for KIAA0918 may be produced in accordance with the procedures described above. The monoclonal antibody specific for KIAA0918 may be contacted with the heterogeneous cell suspension by adding the antibody to the cell suspension under conditions and for a time suitable for antibody binding. Appropriate binding conditions (e.g., temperature, pH, and salt concentration) are readily determinable by the skilled artisan. Cells to which the monoclonal antibody is bound then may be separated from the heterogeneous cell suspension using one of the various methods of separation known in the art.

In the method of the present invention, the appropriate method of separation will depend on the degree of enrichment of hematopoietic stem cells which is desired, as well as the ease, efficacy, efficiency, and speed of the separation technique that is employed. Examples of methods of separation include, without limitation, affinity chromatography, flow cytometry, fluorescence-activated cell sorting, and magnetic separation using antibody-coated magnetic beads. It is also within the confines of the present invention that hematopoietic stem cells may be separated from a heterogeneous cell suspension by passing the suspension over a solid support, such as an insoluble organic polymer in the form of a bead, gel, or plate, to which is attached a monoclonal antibody specific for KIAA0918. Examples of suitable solid supports include, without limitation, agarose, cellulose, dextran, polyacrylamide, polystyrene, or other insoluble organic polymers. The monoclonal antibody may further be attached to the solid support through a spacer molecule, if desired.

The method of the present invention further comprises enriching the concentration of hematopoietic stem cells in the cell suspension before contacting the cell suspension with the KIAA0918. The concentration of hematopoietic stem cells may be enriched, for example, through blood fractionation, density gradient separation, flow cytometry, or magnetic bead separation. Magnetic bead separation may be useful for removing numerous lineage-committed cells, such as basophils, eosinophils, mast cells, megakaryocytes, T-cells, and B-cells.

The present invention also discloses a method for assessing gene expression in a sample of tissue or cells, comprising the steps of: (a) obtaining cDNA from the sample; (b) digesting cDNA obtained from the sample with a primary restriction enzyme to produce a primary set of 3'-terminal restriction fragments; (c) separating in the first dimension, by denaturing polyacrylamide gel electrophoresis (PAGE), the 3'-terminal restriction fragments; (d) sequentially treating the 3'-terminal restriction fragments with a set of secondary restriction enzymes, to produce secondary restriction fragments; (e) separating in the second dimension, by PAGE, the secondary restriction fragments, to generate two-dimensional coordinates; and (f) assessing gene expression in the sample by assessing the two-dimensional coordinates. This method, referred to herein as two-dimensional Gene Expression Fingerprinting (2-D GEF), is based on the two-dimensional gel display of 3'-terminal cDNA restriction fragments produced by one primary (first dimension) digestion and several sequential secondary restriction digestions. This sequence of digestion leads to subdivision of the initial cDNA fragment population into many thousands of non-overlapping subsets. As a result, many thousands of individual sequences per cDNA sample can be visualized using this approach, which is also characterized by a high reproducibility and predictable spatial location of cDNA fragments on two-dimension gels. The 2-D GEF procedure is advantageous because it permits the assessment of gene expression in two ways: (i) it allows global analysis of gene expression; and (ii) it facilitates the discovery of new genes.

In the method of the present invention, cDNA from a tissue or cell sample may be obtained by any method known to one of skill in the art, including isolation of RNA followed by first- and second-strand synthesis of cDNA. Isolation of RNA from cells is well known in the art, and may be accomplished by a number of techniques. For example, whole cell RNA may be extracted using guanidine thiocyanate; cytoplasmic RNA may be prepared by using phenol extraction methods or an RNAgents kit (Promega); and polyadenylated RNA may be selected using oligo-dT cellulose. Thereafter, double-stranded cDNA may be synthesized, extracted, and precipitated, according to methods well known in the art. First-strand cDNA synthesis may be performed using a one-base anchored 5'-biotinylated oligo (dT)-containing primer, followed by second-strand synthesis using the RNaseH-DNA polymerase I protocol [15].

In the method of the present invention, cDNA obtained from a tissue sample is digested with a primary restriction enzyme, such as a four-base-recognition primary restriction enzyme, to produce a primary set of 3'-terminal cDNA restriction fragments. This set of fragments may be selected by binding to Streptavidin beads, then ligated to a double-stranded adapter. Following PCR amplification with biotinylated oligo(dT) and adapter primers, this primary set of 3'-terminal restriction fragments is then separated in the first dimension, according to size, by denaturing PAGE.

For transfer to the second dimension, the gel lane containing biotinylated cDNA fragments may be cut into slices. The slices then may be treated in separate wells of a microliter plate. For example, they may be eluted, bound to Streptavidin beads, and rendered double-stranded by a Sequenase synthesis initiated from a highly-labeled adapter primer. The cDNA fragments then are treated sequentially with a set of restriction enzymes to liberate subpopulations of secondary restriction fragments. The secondary restriction fragments are then separated in the second dimension, by PAGE; thereafter, they may be analyzed on separate gels. Restriction enzymes suitable for the method of the present invention may be selected in such a way as to produce relatively similar numbers of liberated fragments per each round of restriction digestion. Examples of restriction enzymes suitable for primary and secondary digestion include, without limitation, ApaL1, AvaII, EcoR1, EcoRV, Hinf1, Msp1, NdeII, Nsi1, Pst1, SacII, Sty1, and Xba.

In one embodiment of the present invention, the secondary restriction fragments may be separated in the second dimension by standard two-dimensional gene expression fingerprinting format. In a standard 2-D GEF format, intended for the global analysis of gene expression in one cDNA sample, all fragments liberated by a given enzyme are loaded onto one gel to generate a 2-D-like pattern of bands. Alternatively, the secondary restriction fragments may be separated in the second dimension by quasi-two-dimensional gene expression fingerprinting (quasi-2-D GEF). This format is preferable for comparative analysis of gene expression in two or more cell samples. In quasi-2-D GEF, cDNA fragments originating from the same size fraction of the first-dimension gel, but from different cell samples, are loaded side-by-side on each gel.

Following separation of the secondary restriction fragments in the second dimension, to generate two-dimensional coordinates, gene expression in the tissue sample is assessed by assessing the two-dimensional coordinates so generated. In one embodiment of the present invention, gene expression may be assessed using computer-assisted prediction of two-dimensional coordinates of cDNA fragments. Due to the excellent resolving power of the 2-D GEF procedure, the identity of bands on the second-dimension (2-D) gels may be established on the basis of their two-dimensional coordinates. In this regard, it is possible to create software simulating the 2-D GEF procedure.

For example, sequences obtained from a gene database, such as the NCBI UniGene database, may be subjected to computer-simulated primary and sequential secondary digestions, to generate a subdatabase of predicted two-dimensional coordinates for all known human genes. It is contemplated herein that such a subdatabase would be useful for establishing the correspondence between known genes and bands on the 2-D gels. This procedure may be performed in numerous ways, including the following: (i) from database to the gel: identification of fragments on 2-D gels which correspond to selected known genes; or (ii) from gel to the database: identification of genes in the database which might correspond to selected fragments on the 2-D gels. Use of the 2-D GEF procedure in combination with computer software permits a computer-based sampling of existing databases for possible matches with a given fragment detected in a tissue sample, and permits identification of cDNA fragments solely on the basis of their two-dimensional coordinates.

In another embodiment of the present invention, gene expression may be assessed using an expressed sequence tag (EST) derived from an EST clone collection. For example, the 2-D GEF gel patterns of the present invention easily can be compared against the sequence information in an EST database for a given organism, permitting identification in digested cDNA obtained from a tissue sample of a particular EST, including one used as a genetic marker. Comparison between the 2-D GEF gel patterns and the sequence information in an EST also may reveal fragments likely to represent novel mRNAs that have not yet been characterized.

The 2-D GEF method of the present invention permits global analysis of gene expression, and facilitates the discovery of new genes. Furthermore, 2-D GEF allows for comparative assessments of gene expression by comparing the two-dimensional coordinates generated from one particular DNA sample, cell sample, or tissue sample with those generated by a second DNA sample, cell sample, or tissue sample. Moreover, as disclosed herein, the 2-D GEF procedure may be used as an in vitro diagnostic method for detecting the presence of a target cell in a tissue sample, by permitting identification of a genetic marker for the desired target cell. For example, detection of expression of KIAA0918 in a tissue sample may indicate the presence in the tissue sample of hematopoietic stem cells, in accordance with the claimed invention.

The present invention is described in the following Experimental Details section, which is set forth to aid in the understanding of the invention, and should not be construed to limit in any way the scope of the invention as defined in the claims which follow thereafter.

Experimental Details

1. Introduction

Analysis of differential gene expression is important for understanding a number of key biological processes, including proliferation, differentiation, and development. Various approaches for comparative analysis of gene expression, and for identification of differentially-expressed genes, have been proposed. Most widely-used procedures are based on subtractive hybridization [1, 2] or gel display of arbitrarily-primed RT-PCR fragments [3, 4]. Previously, the inventors developed the Gene Expression Fingerprinting (GEF) technique [5–7], which was based on the creation of non-overlapping sets of 3'-terminal cDNA restriction fragments that are displayed by a high-resolution polyacrylamide gel electrophoresis (PAGE). Different variants of cDNA restriction-fragment gel displays were later proposed by other authors [8–10]. Another approach to comparative analysis of gene expression, Serial Analysis of Gene Expression (SAGE), is based on analysis of short, concatenated nucleotide sequence tags; it allows detailed analysis of thousands of transcripts [11]. Integration of principles of subtractive hybridization and 3'-end cDNA restriction-fragment analysis for genome-wide gene analysis also has been suggested [12]. With the development of micro-miniaturization techniques, and the availability of a large number of expressed sequence tag (EST) clones, microchip-based hybridization analysis of global gene expression patterns became possible [13].

In the present experiment, the inventors have developed a new procedure: two-dimensional Gene Expression Fingerprinting (2-D GEF). 2-D GEF builds on the previously-developed variant of the GEF procedure [6, 7] by introducing a first-dimension PAGE for additional subdivision of the primary set of cDNA into a large number of size fractions. This system offers a dramatically-increased resolution, as well as a number of other advantages which were validated in this experiment by analysis of global and differential gene expression in the closely-related Kg-1 and Kg-1a cell lines that were chosen as a model system.

2. Materials and Methods

All standard DNA and RNA manipulations were performed as previously described [14].

a. RNA isolation

Kg-1 and Kg-1a cell lines were obtained from the ATCC. Cell expansion was performed according to the manufacturer's recommendations. Total RNA from about $10^8$ cells of each line was prepared using RNAgents kit (Promega), according to the manufacturer's protocol. The yield was 820 µg for Kg-1 cells and 656 µg for Kg-1a cells.

b. First- and second-strand synthesis

For the first-strand cDNA synthesis, 4.5 µg of total RNA, 15 pmol of BioAd1#T15 primer (5' biotin-GGAATGCCTACCT15-A/G/C) (SEQ ID NO:1), 4 µl of 5×SuperScript buffer (Gibco-BRL), 2 µl of 100 mM DTT, and 1 µl of dNTPs (10 mM each) were combined in a total volume of 19 µl. The mixture was incubated at 75° C. for 2 min, and at 46° C. for 3 min. The reaction was performed with 1 µl (200 units) of SuperScript II (Gibco-BRL) at 46° C. for 1 h. For the second-strand cDNA synthesis, 3 µl of dNTPs (10 mM each), 10 units of E. coli DNA ligase (Gibco-BRL), 40 units of E. coli DNA polymerase I (Gibco-BRL), 2 units of E. coli RNaseH (Gibco-BRL), and a second-strand synthesis buffer (Boehringer, Mannheim, Germany) were added to make a total volume of 100 µl. This reaction mixture was incubated at 16° C. for 2 h. Double-stranded cDNA was extracted with phenol, and precipitated with 1 volume of isopropanol.

c. Preparation of a primary set of 3' cDNA fragments

Double-stranded cDNA was digested with 7.5 units of NdeII (Boehringer, Mannheim, Germany) for 3 h at 37° C. in a total volume of 30 µl. M280 Streptavidin magnetic beads (Dynal) were washed with 1×WBT buffer (10 mM Tris-HCl, pH8.0; 170 mM NaCl; 1 mM EDTA; 0.1% Tween 20), treated with 100 µg of yeast tRNA for 15 min at room temperature, and washed again. The beads were mixed with NdeII-digested cDNA in 1×WBT, incubated for 2 h at room temperature with agitation, then washed to remove unbound fragments. cDNA on the beads was ligated with 50 pmol of double-stranded adapter obtained by annealing of AD#MS/Cmod primer (5'-CGTGGGCTCCAAGCTTCAAATAAACC) (SEQ ID NO:2) and AD#Sau/Wmod primer (5'-GATCGGTTTATTTGAAGCTTGGAGCCCACG) (SEQ ID NO:3), using 6 units of E. coli DNA ligase (Boehringer, Mannheim, Germany) in a 30-µl reaction at 16° C. for 3 h. The beads were washed twice with 1×WBT and once with 1×WB (10 mM Tris-HCI, pH 8.0; 170 mM NaCl; 0.1 mM EDTA), and were finally suspended in 32 µl of TE (10 mM Tris-Cl; 0.2 mM EDTA), pH 8.0.

PCR amplification of 3'-terminal cDNA fragments was performed in a total volume of 50 µl using Advantage cDNA Polymerase Mix (Clontech), 17 pmol of BioAd1#T15 primer, and 17 pmol of AD#MS/Cmod primer, according to the manufacturer's recommendations. 3 µl of cDNA template were amplified for 15 cycles. After initial preheating at 95° C. for 35 sec, amplification was performed as follows: denaturation for 25 sec at 94° C., annealing for 45 sec at 60° C., and elongation for 2.5 min at 70° C.

d. First-dimension PAGE

Ad#MS/C primer (50 pmol) was labeled using 100 µCi of $\gamma^{32}$ P-ATP (6000 Ci/mmol, Amersham) and 10 units of T4 polynucleotide kinase (Boehringer, Mannheim, Germany) in 20 µl for 30 min at 37° C. Non-incorporated radioactivity was removed by passage through the Micro Bio-Spin 6 column (Bio-Rad).

For the first-dimension PAGE, 5 µl of cDNA from the previous step were re-amplified, in a total volume of 200 µl, by 8 cycles of PCR under conditions described above (except that labeled Ad#MS/C primer, diluted five-fold with cold primer, was used). Amplified cDNA was extracted with phenol and precipitated with isopropanol, then dissolved in 5 μl of TE. 10 μl of formamide stop solution were added, and DNA was denatured by incubation at 100° for 1.5 min and resolved by electrophoresis in 6% 1×TBE-7 M Urea denaturing polyacrylamide gel (acrylamide:bisacrylamide=19:1). A 50-bp ladder (Gibco-BRL) labeled with $\gamma^{32}$P-ATP was used as a size marker. Electrophoresis was performed at 1000 V for 2.5 h.

After the run, one glass plate was removed; the gel was covered with Saran Wrap, and then exposed for up to 2 h at +5° C. Gel lanes encompassing cDNA sizes between 100 bp and 1000 bp were each cut into 96 equal slices, and placed in the consecutive wells of the 96-well PCR plate. The cDNA was eluted overnight at room temperature in TE (pH 8.0). Eluates (60 μl) then were transferred to 8-tube PCR strips.

e. Preparation of the samples for secondary restriction endonuclease digestion 3 mg of Streptavidin beads (Dynal) were washed with 1×WBT, treated with 100 μg of yeast tRNA for 15 min at room temperature in 1×WBT, washed once, and suspended in 1 ml of 6×WBT. Subsequent steps were taken with series of 64 samples (32 for each KG-1 and KG-1a cDNA sample). Washes and incubations were performed in 8-tube PCR strips using 8-channel micropipets. For washing, 100 μl of buffer were placed in each well of the strip. Strips were placed on the 96-well magnet (Dynal), and agitation of beads was performed by hand or by transferring the strips in the neighboring columns of the magnet.

Eluted cDNA fragments were bound to 12 μl of a Streptavidin bead suspension for 2 h at room temperature, followed by washing in 1×WBT. Streptavidin beads were incubated for 5 min in 45 μl of denaturing buffer (100 mM NaOH; 1 mM EDTA), and washed in 1×WBT (three times), 1×WB, 15 μl of 1×Sequenase buffer, 0.2 mM dNTPs, and 5 mM DTT. Labeled Ad#MS/C primer (1.3 pmol) was annealed with cDNA template at 45° C. for 25 min in a total volume of 8 μl of 1×Sequenase buffer. 2 μl (3.25 units) of Sequenase version 20 (Amersham), diluted 8-fold in the Sequenase dilution buffer, were added, and the second-strand synthesis was performed for 6 min at room temperature and 15 min at 37° C. Beads were washed with 1×WBT and 1×WB.

f. Restriction endonuclease cycle

Streptavidin beads with immobilized cDNA fragments were treated sequentially with 8 units each of the restriction enzymes listed below, in a total volume of 8 μl. Incubation with restriction endonuclease was performed in a buffer provided by the manufacturer (New England Biolabs) at 37° C. for 60 min, with agitation every 10 min. Supernatants containing liberated fragments were transferred to 96-well PCR plates, and beads were washed with 1×WBT (twice) and with 1×WB prior to the next enzyme treatment.

Restriction enzymes EcoRV, Xba1, ApaL1, Nsi1, Stu1, Pst1, Sty1, and Msp1 were used for the middle third of the first dimension (150–270 b), and SacII, EcoRV, ApaL1, Nsi1, EcoR1, Pst1, Sty1, Msp1, AvaII, and Hinf1 were used for the upper third (270–1000 b). The restriction enzymes and their order were selected on the basis of a computer simulation of the GEF procedure, the aim of which was to obtain a more even distribution of the number of fragments liberated per digestion cycle.

g. Second-dimension PAGE

Fragments released after each restriction enzyme treatment (7.5 μl) were mixed with 1.5 μl of formamide stop solution, denatured and concentrated by incubation at 100° C. for 10 min with lids open, and resolved by electrophoresis in 6% denaturing 1×TBE-7M urea polyacrylamide gel. SequaMark™ (Research Genetics) was $^{32}$P labeled according to the manufacturer's recommendations, and used as a size marker for the second-dimension (2-D) gels. To facilitate handling, the gel was covalently fixed to one of the glass plates by the Bind-Silane (Pharmacia) treatment. Gels were electrophoresed for 2.5 to 3 h at 60 W until the bromophenol blue dye had reached the end of the gel. The gel was soaked in 10% acetic acid for 45 min with agitation, air-dried, and exposed for 1 to 5 days at room temperature using Kodak BioMax film.

h. Recovery of the cDNA fragments from the gel

The cDNA fragments were eluted from the second-dimension gel in the elution buffer (150 mM NaCl; 10 mM Tris-HCl, pH 8.0; 0.2 mM EDTA; tRNA 100 μg/ml) at 65° C. for 2 h, precipitated with 3 vol of ethanol, and oligo(dG)-tailed using 20 units of terminal transferase (Gibco-BRL), 1.5 mM dGTP, and a buffer supplied by the manufacturer, for a total volume of 20 μl. cDNA fragments were amplified by PCR using Advantage cDNA Polymerase Mix (Clontech), 20 pmol of C13 primer (5'-AAGGAATTCCCCCCCCCCCCC-3') (SEQ ID NO:4), and 20 pmol of Ad#MS/Cmod primer for 40 cycles: 60 sec at 95° C., 60 sec at 60° C., and 60 sec at 70° C. The PCR fragments were purified through agarose gel, and sequenced directly. For cloning, the PCR fragments were treated with EcoR1 and NdeII, and inserted into pBlueScript KS plasmid (Stratagene).

i. Northern blot analysis

20 μg of total RNA from KG-1 and KG-1a were resolved on a 1.2% formaldehyde agarose gel, transferred onto Hybond-N nylon membrane (Amersham), and probed with $^{32}$P-labeled inserts carrying cloned cDNA fragments or corresponding ESTs. EST clones used for hybridization were obtained from Genome Systems, and their identities were verified by sequencing.

3. Results and Discussion a. The 2-D GEF protocol

The scheme of the 2-D GEF procedure is presented in FIG. 1. First-strand cDNA synthesis is performed using a one-base anchored 5'-biotinylated oligo(dT)-containing primer, followed by second-strand synthesis using the RNaseH-DNA polymerase I protocol [15]. After digestion with a four-base recognition primary restriction enzyme, 3'-terminal cDNA fragments are selected by binding to Streptavidin beads, and ligated to a double-stranded adapter. Following PCR amplification with biotinylated oligo(dT) and adapter primers, this primary set of 3'-terminal restriction fragments is separated according to size by denaturing PAGE.

For transfer to the second dimension, the gel lane containing biotinylated cDNA fragments is cut into 96 slices, which are then treated in separate wells of a microliter plate: they are eluted, bound to the Streptavidin beads, and rendered double-stranded by a Sequenase synthesis initiated from the highly-labeled adapter primer. cDNA fragments immobilized on the Streptavidin beads are treated sequentially with a set of restriction enzymes to liberate subpopulations of secondary restriction fragments. These fragments then are analyzed on separate gels by electrophoresis. Restriction enzymes are selected in such a way as to produce relatively similar numbers of liberated fragments per each round of restriction digestion.

Figure 2:
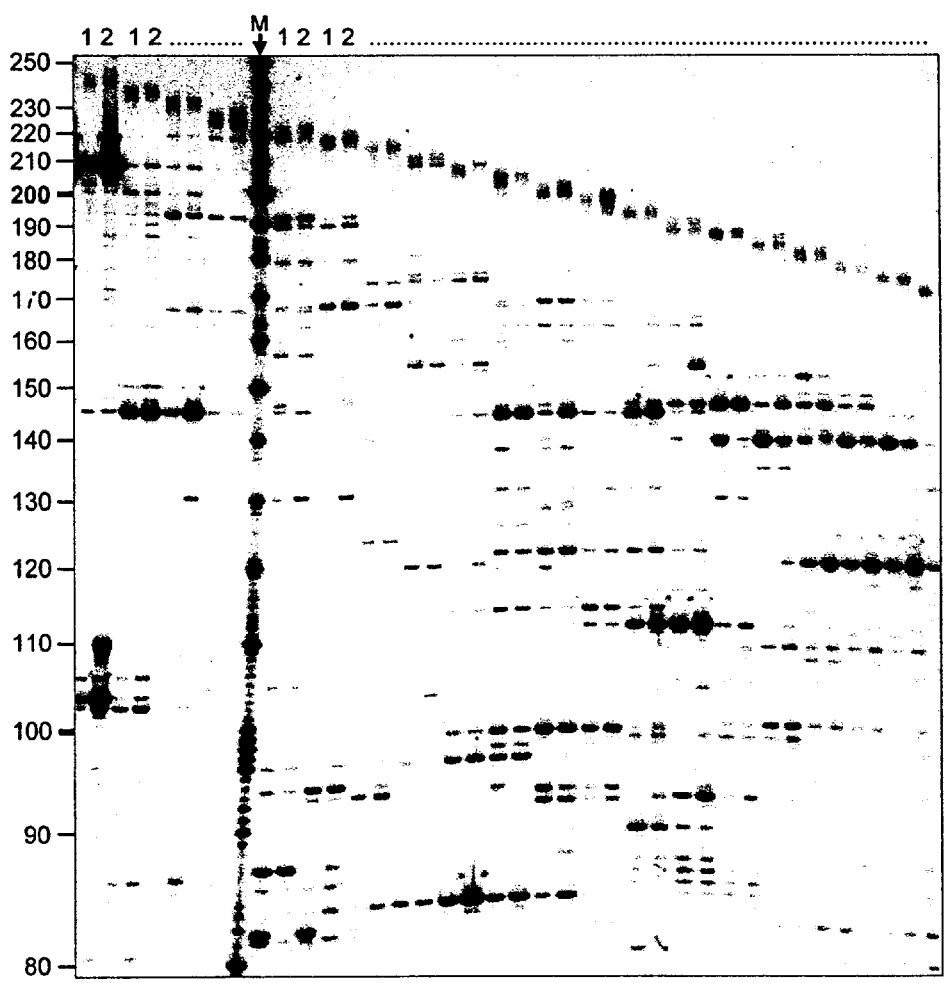
FIG. 2 illustrates a region of the second-dimension polyacrylamide gel electrophoresis (PAGE) performed in the quasi-2-D format. cDNA and samples from Kg-1 (lane 1) and Kg-1a (lane 2) cell lines were loaded side-by-side. The picture presented in the figure was generated by the Sty1 restriction enzyme treatment. Prior to Sty1, the cDNA on beads was treated sequentially with EcoRV, Xba1, ApaL1, Nsi1, Stu1, and Pst1. The arrow indicates the SequaMark™ (Research Genetics) marker lane. Positions of selected SequaMark bands are indicated on the left side; it should be noted, though, that this marker provides 1 base resolution for lengths ranging from 40 to 400 bases.

Two different formats of second-dimension gels have been established. In a standard 2-D GEF format, intended for the global analysis of gene expression in one cDNA sample, all fragments liberated by a given enzyme are loaded onto one gel to generate a 2-D-like pattern of bands (not shown). Another format, quasi-2-D GEF, is preferable for comparative analysis of gene expression in two or more cell samples (FIG. 2). In quasi-2-D GEF, cDNA fragments originating from the same size fraction of the first-dimension gel, but from different cell samples, are loaded side-by-side on each gel.

b. Testing the approach

The inventors have applied the 2-D GEF procedure to analyze gene expression in two closely-related human myeloid cell lines: Kg-1 and Kg-1a. The latter line is a more-undifferentiated subline of the former [16, 17]. Primary restriction digestion was performed with NdeII endonuclease, followed by sequential digestion with eight restriction enzymes for the middle portion of the first-dimension gel, and ten enzymes for the upper portion of the first-dimension gel (Table 1). The quasi-2-D variant was used for the second-dimension gels. The average number of bands per second-dimension (2-S) gel was found to be close to 200 for the middle portion (150–270 bp) and 570 for the upper portion (270–1000 bp) of the first-dimension gel. The analysis encompassed approximately 50% of the mRNA population (see below), and the number of fragments displayed on all 2-D gels together was 7,300 for each cell line. Therefore, estimates suggest that each of these cell lines contains about 15,000 independent mRNA species.

Inspection of half of the resulting eighteen 2-D gels (3,650 bands per cell line) revealed a total of 74 fragments, demonstrating substantial differential distribution (more than 3-fold difference in intensity) between the two cell lines. Therefore, the candidate differentially-expressed mRNAs constituted about 1% (37 vs. 3,650) of the total number of mRNAs expressed in these cells. On the basis of the relative signal intensity, the majority of these candidate sequences represented moderately- to weakly-expressed RNAs.

TABLE 1

An example of the enzyme set for the secondary restriction digestion

| Endonuclease | Individual, % | Overlap, % | Total, % |
|---|---|---|---|
| SacII (CCGC/GG) | 3.12 | 0.00 | 3.12 |
| EcoRV (GAT/ATC) | 4.26 | 0.22 | 7.38 |
| ApaL1 (G/TGCAC) | 6.37 | 1.09 | 13.75 |
| Nsi1 (ATGCA/T) | 7.40 | 2.25 | 21.15 |
| EcoR1 (G/AATTC) | 5.96 | 3.21 | 27.11 |
| Pst1 (CTGCA/G) | 11.82 | 8.34 | 38.93 |
| Sty1 (C/CWWGG) | 14.42 | 19.24 | 53.35 |
| Msp1 (C/CGG) | 8.18 | 23.68 | 61.53 |
| AvaII (G/GWCC) | 5.32 | 30.87 | 66.85 |
| Hinf1 (G/ANTC) | 9.65 | 43.83 | 76.50 |

Individual: the percentage of cDNA fragments predicted to be liberated by the current endonuclease; Overlap: the percentage of cDNA sequences sharing cleavage sites for the current and previous restriction enzymes; Total: the cumulative percentage of cDNA fragments cleaved after the current and previous restriction cycles c. Verification of candidate sequences Twenty-five candidate differentially-expressed sequences were recovered from the gel, amplified, and then directly sequenced. BLAST analysis [18] revealed 100% identity with ESTs for four cDNA fragments. Six cDNA fragments did not show any matches with the sequence database. One fragment revealed homology with a sequence belonging to an Alu repeat subfamily. The other fourteen fragments corresponded to known genes described in Table 2. Among these genes, those encoding beta and gamma chains of MHCII molecules were previously known to be expressed in Kg-1, but not in Kg-1a, cells [17]. Three fragments originated from highly-expressed ribosomal protein mRNAs. Sequence analysis indicated that, for at least two of them, this was apparently caused by procedural artifacts.

TABLE 2

Characterization of candidate sequences differentially expressed in Kg-1 and Kg-1a cell lines

| Band # | Kg-1 | Kg-1a | Homology | Reproducibility | Verification | Northern | RT-PCR |
|---|---|---|---|---|---|---|---|
| NB16 | − | + | KIAA0918 | Yes | Differential | Yes | N.D. |
| NB63 | − | + | EST | N.D. | Differential | Yes | N.D. |
| NB64 | − | + | EST | N.D. | Differential | Yes | N.D. |
| NB66 | − | + | EST | N.D. | Differential | Yes | N.D. |
| NB67 | + | − | MHCII gamma chain | N.D. | Differential | Yes | N.D. |
| NB68 | + | − | ALDH1 | N.D. | Differential | Yes | N.D. |
| NB69 | − | + | No hits found | N.D. | Differential | No signal | Yes |
| NB70 | − | + | NB101 = Uncx4.1* | N.D. | Differential | N.D. | N.D. |
| NB71 | − | + | No hits found | N.D. | Differential | No signal | Yes |
| NB72 | − | + | No hits found | N.D. | Non differential | Yes | N.D. |
| NB91 | + | − | MHCII beta chain | Yes | Differential | Yes | N.D. |
| NB95 | − | + | Alu repeats | Yes | N.D. | N.D. | N.D. |
| NB96 | − | + | hKCa4 | Yes | Differential | Yes | N.D. |
| NB97 | − | + | ZEB | N.D. | Non differential | Yes | N.D. |
| NB101 | − | + | mouse Uncx4.1* | Yes | Differential | Yes | Yes |
| NB103 | + | − | No hits found | Yes | Differential | No signal | Yes |
| NB104 | − | + | No hits found | Yes | N.D. | N.D. | N.D. |
| NB106 | + | − | ribosomal protein L9 | No | Non differential | Yes | N.D. |
| NB108 | − | + | ribosomal protein L10 | No | Non differential | Yes | N.D. |
| NB109 | + | − | No hits found | N.D. | Differential | No signal | Yes |
| NB110 | + | − | EST | N.D. | N.D. | N.D. | N.D. |
| NB111 | + | − | ribosomal protein L27 | No | Non differential | Yes | N.D. |
| NB112 | + | − | claudin 10 | Yes | Differential | Yes | N.D. |
| NB113 | − | + | Jagged-1 | Yes | Differential | Yes | N.D. |
| NB114 | − | + | TALLA-1 | Yes | Differential | Yes | N.D. |

+ or − indicates relative expression level in two cell lines inferred from the 2-D GEF experiment.
In the last two columns, Yes indicates that a reliably detectable signal on a Northern blot or in an RT-PCR experiment was obtained for a given sequence.
N.D. = no data available;
*= only part of the NB101 sequence shows high homology to mouse Uncx4.1

Figure 3:
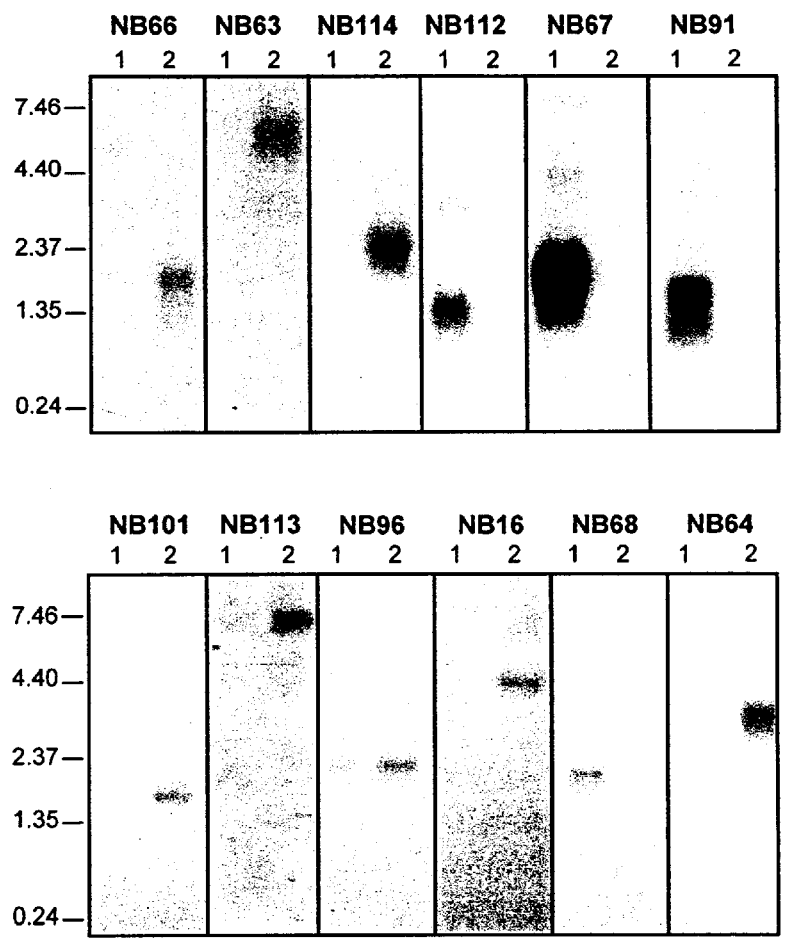
FIG. 3 sets forth a Northern blot analysis of total RNA isolated from Kg-1 and Kg-1a cell lines. Equal amounts of total RNA (20 μg) were loaded into lanes 1 (Kg-1) and 2 (Kg-1a). Blots were hybridized with $^{32}$P-labeled cloned probes, corresponding to fragments NB66 (EST AA428186), NB63 (EST H11385), NB114 (EST H93036), NB112 (EST AA142937), NB67 (EST AA617864), NB91 (EST AA573912), NB101 (obtained using 3' rapid amplification of cDNA ends (RACE) procedure), NB113 (EST AI144181), NB96 and NB16 (both obtained using RT-PCR with two specific primers), NB68 (EST AI050734), and NB64 (EST AA814890). Positions of 0.24- to 9.5-Kb RNA ladder bands (Gibco-BRL) are indicated on the left side. The 9.5-kb band is not shown.

To verify the expression pattern of candidate sequences, Northern blot hybridization was performed with total RNA from KG-1 and KG-1a cell lines. Twelve of twenty-one candidate sequences confirmed the expected differential expression pattern (FIG. 3). Four sequences did not show a signal on Northern blots, but their expression patterns were confirmed by a more sensitive reverse-transcription PCR (RT-PCR) technique (data not shown). Five clones, including all three corresponding to ribosomal proteins, were not differentially expressed. Therefore, the percentage of the false-positive fragments was approximately 25%. In summary, these results demonstrate the high efficiency and reliability of the 2-D GEF procedure for identification of differentially-expressed genes. These advantages obviate the need for duplicate samples commonly required for such techniques as differential mRNA display.

In comparing gene expression patterns in primitive human hematopoietic Kg-1 and Kg-1a cell lines, as described above, the inventors identified a number of genes expressed specifically in one cell line or the other. In particular, one of the genes was found to be identical to the previously-sequenced human KIAA0918 gene, a use for which was unknown prior to the present experiment. Prediction of the amino acid sequence for KIAA0918 indicates that its product belongs to a class of transmembrane, presumably cell surface, proteins. Because the gene is expressed in the more primitive Kg-1a cell line, which is close to a human hematopoietic stem cell line, this gene may be used as a genetic marker for identification of human hematopoietic stem cells.

d. Reproducibility of the 2-D GEF procedure

To rigorously test the reproducibility of the 2-D GEF procedure, the 2-D GEF experimental protocol, including the cDNA synthesis, was repeated, beginning with the same RNA preparation. The 2-D gels derived from the middle portion of the first dimension (150–270 pb) were compared for two independent experiments. Corresponding bands differing in intensity more than three-fold were ranked as non-reproducible. The reproducibility from gel to gel varied from 92 to 100% of total bands, with an average of 95.4%. It appears that a substantial part of the apparent non-reproducibility was caused by the difficulty in achieving a perfectly-identical subdivision of the first-dimension strip into size fractions for experiments separated in time. The reproducibility of fragments distributed differentially between the two cell lines was also high, with about 90% of the differential fragments reproducible between two independent experiments.

When cDNA synthesis and 2-D analysis were performed in parallel on duplicate samples, the reproducibility, as expected, increased markedly, reaching 99.5–100%. The results of the verification of candidate differentially-expressed sequences described above also support these data, since the reported low percentage of false positives (c.a. 25%) may only be obtained if the degree of non-reproducibility in the experiment was several-fold lower than the percentage of differentially-expressed sequences (1%).

e. Computer simulation of 2-D GEF

The excellent resolving power of the 2-D GEF procedure prompted the inventors to ascertain whether the identity of bands on the 2-D gels could be established on the basis of their two-dimensional coordinates. To this end, the inventors created software simulating the 2-D GEF procedure. Sequences obtained from the NCBI UniGene database were subjected to computer-simulated primary and sequential secondary digestions, to generate a subdatabase of predicted two-dimensional coordinates for all known human genes. This subdatabase can be used to establish the correspondence between known genes and bands on the 2-D gels. This procedure might be performed in two ways: (i) from the database to the gel: identification of fragments on 2-D gels which correspond to selected known genes; or (ii) from the gel to the database: identification of genes in the database which might correspond to selected fragments on the second-dimension gels.

Computer simulation of the GEF procedure was performed using sequence information from 7,459 known human genes. Approximately 97% of these cDNA sequences can be digested with NdeII. Approximately 5% of these NdeII-digested cDNA fragments are too short (less than 20–30 bp), and are poorly suited for analysis, since only a small percentage contains sites for secondary restriction enzymes. The primary cDNA fragments longer than 1,000 bp (c.a. 8% of total digested cDNA) are relatively inadequate for analysis, due to the reduced resolution of the first-dimension gel in this range of lengths. Therefore, prior to the secondary restriction digestion stage, at least 8%, and up to 15%, of the cDNAs are excluded from the analysis. Similar estimates were obtained when Nla III or Mae III was used as the primary enzyme (up to 11.5% and 15.5%, respectively).

The computer analysis indicates that, during the secondary digestion stage, 10 to 15 digestion cycles should normally liberate 80–95% of cDNA fragments. Thus, the theoretical estimates show that approximately 70–85% of the total mRNA population can be analyzed by the 2-D GEF procedure, using one primary enzyme. However, for the nearly-complete (95% or more) analysis of cellular mRNAs, two different primary enzymes should be used. In the present experiment, the inventors have analyzed and resolved approximately 50% of the total mRNA population.

f. Prediction ability of the software

To explore the prediction power of the 2-D GEF software, sixteen fragments were recovered from the gels, amplified, and sequenced without prior cloning (Table 3). Eleven of the fragments corresponded to the predicted sequences. For one fragment, an incorrect prediction was made, due to the absence of the corresponding sequence (mitochondrial 16S ribosomal RNA) in the database. For four fragments, no correct matches in the database were found. Sequencing of these fragments revealed their identities as known genes. In most cases, the reason why sequences were not identified correctly related to flaws in the Unigene database, e.g., sequence mistakes, an absence of complete 3' sequence, or an absence of the sequence in the database (Table 3). In only one case out of five (ribosomal protein L27), the failure to correctly identify the sequence was due to an artifact in the GEF procedure itself.

In an earlier 2-D GEF experiment, performed using a suboptimal cDNA synthesis protocol, twenty fragments with matches in the human cDNA database were analyzed. Fourteen fragments were found to correspond to the correct prediction. Two other bands had more than one match in the database, and corresponded to one of them. Three more bands arose due to a cDNA synthesis artifact which was later eliminated. Only one band did not correspond to the predicted sequence in the database. The reason for this mistake was the lack of information on the 3'-untranslated region of the corresponding sequence in the cDNA database.

TABLE 3

Prediction of the identity of the cDNA fragments on the basis of their 2-D GEF coordinates

| Band | Identity | Prediction | Source of the problem |
|---|---|---|---|
| NB1 | 16S mitochondrial RNA | wrong | DB: sequence absent |
| NB2 | ribosomal protein S29 | correct | |
| NB3 | ribosomal protein L23 | correct | |
| NB4 | KIAA0178 | correct | |
| NB5 | KIAA0190 | correct | |
| NB6 | transl. controlled tumor protein | no match | DB: sequence error |
| NB91 | MHC class 11 DR-beta-111 | correct | |
| NB67 | MHC class 11 gamma-chain | correct | |
| NB114 | TALLA-1 | correct | |
| NB97 | zinc finger protein ZEB | no match | DB: 3' sequence absent |
| NB112 | putative OSP-like protein | correct | |
| NB96 | hKCa4 | no match | DB: sequence absent |
| NB68 | Aldehyde dehydrogenase 1 | correct | |
| NB113 | Jagged 1 | correct | |
| NB111 | ribosomal protein L27 | no match | 3rd GATC site cleaved |
| NB106 | ribosomal protein L9 | correct | |

The second experiment is shown. Summary of results for first experiment: 70% = correct; 10% = more than one match; 15% = GEF artifacts (cause eliminated later); and 5% = database errors. Summary of results for second experiment: 69% = correct; 6% = GEF artifacts; and 25% = database errors. DB = database g. Problems and further optimization The major improvement in the present experiment arose from the use of the RNaseH/DNA polymerase cDNA synthesis protocol [15], which significantly increased reproducibility over that of previous GEF variants [6, 7]. However, the differing densities of fragments liberated from the lower and upper portions of the first dimension is one of the drawbacks of the 2-D GEF procedure. Separation into gel slices, with a regular increase in the linear size of the slice from top to bottom, will substantially alleviate this problem. Several artifacts were also detected and eliminated during the establishment of the procedure.

One potentially important, but so far rarely encountered, artifact is the annealing of the (T)-primer on oligo(dA)-containing stretches upstream of the poly(A) tail during the first-strand synthesis. Such mispriming would lead to the appearance of bands not predicted by computer simulation of the 2-D GEF method, and might be a major source of non-reproducibility in the procedure. Increasing the temperature in the first-strand synthesis to 46° C. reduces the significance of this artifact. Using yet more stringent conditions for annealing and synthesis in the presence of trehalose stabilizer [19] may essentially suppress this mispriming on all but the longest uninterrupted oligo(dA) stretches. These latter cases, though, would be easily recognized by software means, and might be incorporated in the computer analysis.

Another artifact detected in the present experiment is the incomplete digestion of double-stranded cDNA by the restriction enzymes, particularly in the vicinity of magnetic beads. Although the magnitude of this defect is low, it does represent a problem for highly-expressed genes, such as those encoding ribosomal proteins. In the current protocol, the significance of this artifact was substantially reduced; increasing the length of the oligo(dT)-containing primer is likely to further improve the situation.

h. Potential use of the 2-D GEF procedure

The 2-D GEF method represents a dramatic improvement over the one-dimensional GEF previously developed by the inventors [6]. One of the most significant advantages of 2-D GEF is the high resolution created by the additional subdivision of the CDNA population into approximately 100 size subsets at the first-dimension step. Therefore, it can be estimated, taking into account partial overlap, that each lane of the second dimension may contain, on average, 60- to 80-fold fewer individual cDNA sequences than in the original GEF procedure. The further 10- to 15-fold reduction of the cDNA complexity in the second dimension, due to sequential digestion, decreases the complexity of the population of cDNA fragments 600- to 1200-fold per average lane of the second-dimension gel.

Based on the complexity of the mRNA pool in an average cell type (~10,000–20,000 independent sequences per cell), the inventors have estimated that, on average, 10 to 15 bands per lane might be expected for the middle portion, and approximately 20 to 40 bands per lane for the upper portion, of the first-dimension gel. Therefore, the 2-D GEF procedure should be able to resolve into individual cDNA bands the majority of RNAs expressed in a given cell type. Moreover, given that polyacrylamide gel can resolve 300–500 DNA fragments per lane, the 2-D GEF procedure provides the potential for the unique localization and correct identification of the larger part of the estimated 100,000 human mRNAs.

The high resolution provided by the 2-D GEF procedure also permits analysis of the cDNA fragments by direct sequencing without prior cloning. In comparison with other techniques for gel display of cDNA restriction fragments [8–10], the inventors' procedure provides the highest resolution, and can work reliably with small amounts of starting material. The present experiments have demonstrated that the method may be applied to starting material consisting of merely two thousand sorted cells (not shown). High reproducibility, even between completely independent experiments, provides the potential basis for sharing and comparing 2-D GEF data between different labs, and for establishing databases of 2-D coordinates for cDNA fragments.

One of the major features of 2-D GEF is its ability to facilitate prediction, using computer simulation, of the location on the gel of cDNA fragments. The inventors' data indicate that approximately 70% of cDNA fragments on the 2-D gel can be correctly identified, and that most failures are associated with database errors. In only 6% or less of the cases, the problems could be attributed to the method itself. Therefore, it may be assumed that further accumulation of sequence data and further improvement of the quality of cDNA databases will increase prediction power of the 2-D GEF software to approximately 90–95%. Finally, it should be noted that 2-D GEF provides a very sensitive technique for the detection of gene expression. Some of the sequences differentially expressed in Kg-1/Kg-1a cells were detected by PCR only, not by Northern blot analysis, thereby indicating that they belonged to the low-abundance mRNA class. According to the inventors' estimates, messages expressed at a level of several copies per cell should be readily detected by the 2-D GEF procedure.

The technical developments of the last years, which culminated in the advent of cDNA microarrays [13], have provided an efficient procedure for gene expression analysis on a mass scale. However, these methods depend on cDNA/EST clone collections and existing sequence information and, by themselves, are poorly suited to the identification of novel expressed sequences. For the 2-D GEF approach, no such pre-existing information is necessary. Furthermore, with accumulation of the sequence information in the EST database for a given organism, the 2-D GEF gel patterns easily can be compared against the database to reveal the fragments likely to represent novel mRNAs that have not yet been characterized. Accordingly, the inventors suggest that the most efficient uses of the proposed technique may be gene expression analysis during the initial stages of a genome project for a given organism, as well as searches for novel expressed sequences.

The major bottleneck in the 2-D GEF technique so far is the necessity to perform routine and laborious steps of restriction-enzyme treatments on numerous samples. However, the inventors believe that it is exactly this feature which might provide the basis for automation of the procedure, thereby permitting the performance of an exhaustive global gene expression analysis for a given cell type within a matter of days or weeks.

REFERENCES

1. Hedrick et al., *Nature*, 308:149–153, 1984.
2. Sagerström et al., *Annu. Rev. Biochem.*, 66:751–83, 1997.
3. Welsh et al., *Nucleic Acids Res.*, 20:4965–70, 1992.
4. Liang and Pardee, *Science*, 257:967–71, 1992.
5. Ivanova et al., *Molekuliarnaia Biologia.*, 28:1367–75, 1994.
6. Ivanova and Belyavsky, *Nucleic Acids Res.*, 23:2954–58, 1995.
7. Ivanova and Belyavsky, In *Gene Cloning and Analysis: Current Innovations*, Schaefer, B. C., ed. (Wymondham, U. K.: Horizon Scientific Press, 1997) 43–60.
8. Prashar and Weissman, *Proc. Natl. Acad. Sci. USA*, 93:659–63, 1996.
9. Kato, K., *Nucleic Acids Res.*, 23:3685–90, 1995.
10. Suzuki et al., *Nucleic Acids Res.*, 24:289–94, 1996.
11. Velculescu et al., *Science*, 270:484–87, 1995.
12. Wang and Rowley, *Proc. Natl. Acad. Sci. USA*, 95:119099–14, 1998.
13. Schena et al., *Science*, 270:467–70, 1995.
14. Sambrook et al., *Molecular Cloning: A Laboratory Manual* (Plainview, N.Y.: Cold Spring Harbor Laboratory Press, 1989).
15. Gubler and Hoffman, *Gene*, 25:263–69, 1983.
16. Koeffler and Golde, *Science*, 200:1153–54, 1978.
17. Koeffler et al., *Blood*, 56:263–72, 1980.
18. Altschul et al., *Nucleic Acids Res.*, 25:3389–402, 1997.
19. Mizuno et al., *Nucleic Acids Res.*, 27:1345–49, 1999.
20. Siminovitch et al., *J. Cell. Comp. Physiol.*, 62:327–36, 1963.
21. Jursskova and Tkadlecek, *Nature*, 206:951–52, 1965.
22. Till and McCulloch, *Rad. Res.*, 14:213–22, 1961.
23. Dexter and Spooncer, *Annu. Rev. Cell Biol.*, 3:423–41, 1987.
24. Rao and Dravid, Indian *J. Exp. Biol.*, 37:1051–52, 1999.
25. Beers and Berkow, eds., *The Merck Manual of Diagnosis and Therapy*, $17^{th}$ ed. (Whitehouse Station, N.J.: Merck Research Laboratories, 1999) 961, 968.
26. Benedetti, F., *Tumori*, 82:S3–13, 1996.
27. Baech and Johnsen, *Stem Cells*, 18:76–86, 2000.
28. Dao and Nolta, *Leukemia*, 14:773–76, 2000.
29. Ausubel et al., *Current Protocols in Molecular Biology* (N.Y.: John Wiley and Sons, N.Y., 1997).

All publications mentioned hereinabove are hereby incorporated in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for detecting the presence of hematopoietic stem cells in a heterogeneous cell suspension that may contain hematopoietic stem cells, comprising detecting cells expressing KIAA0918 in the heterogeneous cell suspension, wherein the expression of KIAA0918 is detected using at least one nucleic acid probe which hybridizes to nucleic acid encoding KIAA0918, wherein KIAA0918 comprises the amino acid sequence set forth in SEQ ID NO:5, and wherein the presence of cells expressing KIAA0918 is indicative of the presence of hematopoietic stem cells.

2. The method of claim 1, wherein the nucleic acid probe is labeled with a detectable marker.

* * * * *

SEQUENCE LISTING

<160> NUMBER OF SEQ ID NOS: 6

<210> SEQ ID NO 1
<211> LENGTH: 13
<212> TYPE: DNA
<213> ORGANISM: artificial sequence
<220> FEATURE:
<223> OTHER INFORMATION: primer

<400> SEQUENCE: 1
ggaatgccta cct                                                      13

<210> SEQ ID NO 2
<211> LENGTH: 26
<212> TYPE: DNA
<213> ORGANISM: artificial sequence
<220> FEATURE:
<223> OTHER INFORMATION: primer

<400> SEQUENCE: 2

-continued cgtgggctcc aagcttcaaa taaacc                                               26

<210> SEQ ID NO 3
<211> LENGTH: 30
<212> TYPE: DNA
<213> ORGANISM: artificial sequence
<220> FEATURE:
<223> OTHER INFORMATION: primer

<400> SEQUENCE: 3
gatcggttta tttgaagctt ggagcccacg                                           30

<210> SEQ ID NO 4
<211> LENGTH: 21
<212> TYPE: DNA
<213> ORGANISM: artificial sequence
<220> FEATURE:
<223> OTHER INFORMATION: primer

<400> SEQUENCE: 4
aaggaattcc cccccccccc c                                                    21

<210> SEQ ID NO 5
<211> LENGTH: 958
<212> TYPE: PRT
<213> ORGANISM: Homo sapiens

<400> SEQUENCE: 5

Met His Thr Cys Cys Pro Pro Val Thr Leu Glu Gln Asp Leu His Arg
1               5                   10                  15

Lys Met His Ser Trp Met Leu Gln Thr Leu Ala Phe Ala Val Thr Ser
            20                  25                  30

Leu Val Leu Ser Cys Ala Glu Thr Ile Asp Tyr Tyr Gly Glu Ile Cys
        35                  40                  45

Asp Asn Ala Cys Pro Cys Glu Glu Lys Asp Gly Ile Leu Thr Val Ser
    50                  55                  60

Cys Glu Asn Arg Gly Ile Ile Ser Leu Ser Ile Ser Pro Pro Arg
65                  70                  75                  80

Phe Pro Ile Tyr His Leu Leu Leu Ser Gly Asn Leu Leu Asn Arg Leu
                85                  90                  95

Tyr Pro Asn Glu Phe Val Asn Tyr Thr Gly Ala Ser Ile Leu His Leu
            100                 105                 110

Gly Ser Asn Val Ile Gln Asp Ile Glu Thr Gly Ala Phe His Gly Leu
        115                 120                 125

Arg Gly Leu Arg Arg Leu His Leu Asn Asn Asn Lys Leu Glu Leu Leu
    130                 135                 140

Arg Asp Asp Thr Phe Leu Gly Leu Glu Asn Leu Glu Tyr Leu Gln Val
145                 150                 155                 160

Asp Tyr Asn Tyr Ile Ser Val Ile Glu Pro Asn Ala Phe Gly Lys Leu
                165                 170                 175

His Leu Leu Gln Val Leu Ile Leu Asn Asp Asn Leu Leu Ser Ser Leu
            180                 185                 190

Pro Asn Asn Leu Phe Arg Phe Val Pro Leu Thr His Leu Asp Leu Arg
        195                 200                 205

Gly Asn Arg Leu Lys Leu Leu Pro Tyr Val Gly Leu Leu Gln His Met
    210                 215                 220

Asp Lys Val Val Glu Leu Gln Leu Glu Glu Asn Pro Trp Asn Cys Ser
225                 230                 235                 240

-continued

```
Cys Glu Leu Ile Ser Leu Lys Asp Trp Leu Asp Ser Ile Ser Tyr Ser
                245                 250                 255
Ala Leu Val Gly Asp Val Val Cys Glu Thr Pro Phe Arg Leu His Gly
            260                 265                 270
Arg Asp Leu Asp Glu Val Ser Lys Gln Glu Leu Cys Pro Arg Arg Leu
        275                 280                 285
Ile Ser Asp Tyr Glu Met Arg Pro Gln Thr Pro Leu Ser Thr Thr Gly
    290                 295                 300
Tyr Leu His Thr Thr Pro Ala Ser Val Asn Ser Val Ala Thr Ser Ser
305                 310                 315                 320
Ser Ala Val Tyr Lys Pro Pro Leu Lys Pro Lys Gly Thr Arg Gln
                325                 330                 335
Pro Asn Lys Pro Arg Val Arg Pro Thr Ser Arg Gln Pro Ser Lys Asp
            340                 345                 350
Leu Gly Tyr Ser Asn Tyr Gly Pro Ser Ile Ala Tyr Gln Thr Lys Ser
        355                 360                 365
Pro Val Pro Leu Glu Cys Pro Thr Ala Cys Ser Cys Asn Leu Gln Ile
    370                 375                 380
Ser Asp Leu Gly Leu Asn Val Asn Cys Gln Glu Arg Lys Ile Glu Ser
385                 390                 395                 400
Ile Ala Glu Leu Gln Pro Lys Pro Tyr Asn Pro Lys Lys Met Tyr Leu
                405                 410                 415
Thr Glu Asn Tyr Ile Ala Val Val Arg Arg Thr Asp Phe Leu Glu Ala
            420                 425                 430
Thr Gly Leu Asp Leu Leu His Leu Gly Asn Asn Arg Ile Ser Met Ile
        435                 440                 445
Gln Asp Arg Ala Phe Gly Asp Leu Thr Asn Leu Arg Arg Leu Tyr Leu
    450                 455                 460
Asn Gly Asn Arg Ile Glu Arg Leu Ser Pro Glu Leu Phe Tyr Gly Leu
465                 470                 475                 480
Gln Ser Leu Gln Tyr Leu Phe Leu Gln Tyr Asn Leu Ile Arg Glu Ile
                485                 490                 495
Gln Ser Gly Thr Phe Asp Pro Val Pro Asn Leu Gln Leu Leu Phe Leu
            500                 505                 510
Asn Asn Asn Leu Leu Gln Ala Met Pro Ser Gly Val Phe Ser Gly Leu
        515                 520                 525
Thr Leu Leu Arg Leu Asn Leu Arg Ser Asn His Phe Thr Ser Leu Pro
    530                 535                 540
Val Ser Gly Val Leu Asp Gln Leu Lys Ser Leu Ile Gln Ile Asp Leu
545                 550                 555                 560
His Asp Asn Pro Trp Asp Cys Thr Cys Asp Ile Val Gly Met Lys Leu
                565                 570                 575
Trp Val Glu Gln Leu Lys Val Gly Val Leu Val Asp Glu Val Ile Cys
            580                 585                 590
Lys Ala Pro Lys Lys Phe Ala Glu Thr Asp Met Arg Ser Ile Lys Ser
        595                 600                 605
Glu Leu Leu Cys Pro Asp Tyr Ser Asp Val Val Ser Thr Pro Thr
    610                 615                 620
Pro Ser Ser Ile Gln Val Pro Ala Arg Thr Ser Ala Val Thr Pro Ala
625                 630                 635                 640
Val Arg Leu Asn Ser Thr Gly Ala Pro Ala Ser Leu Gly Ala Gly Gly
                645                 650                 655
```

-continued

```
Gly Ala Ser Ser Val Pro Leu Ser Val Leu Ile Leu Ser Leu Leu Leu
            660                 665                 670
Val Phe Ile Met Ser Val Phe Val Ala Ala Gly Leu Phe Val Leu Val
            675                 680                 685
Met Lys Arg Arg Lys Lys Asn Gln Ser Asp His Thr Ser Thr Asn Asn
    690                 695                 700
Ser Asp Val Ser Ser Phe Asn Met Gln Tyr Ser Val Tyr Gly Gly Gly
705                 710                 715                 720
Gly Gly Thr Gly His Pro His Ala His Val His His Arg Gly Pro
                725                 730                 735
Ala Leu Pro Lys Val Lys Thr Pro Ala Gly His Val Tyr Glu Tyr Ile
            740                 745                 750
Pro His Pro Leu Gly His Met Cys Lys Asn Pro Ile Tyr Arg Ser Arg
            755                 760                 765
Glu Gly Asn Ser Val Glu Asp Tyr Lys Asp Leu His Glu Leu Lys Val
        770                 775                 780
Thr Tyr Ser Ser Asn His His Leu Gln Gln Gln Gln Pro Pro Pro
785                 790                 795                 800
Pro Pro Gln Gln Pro Gln Gln Pro Pro Pro Gln Leu Gln Leu Gln
                805                 810                 815
Pro Gly Glu Glu Glu Arg Arg Glu Ser His His Leu Arg Ser Pro Ala
            820                 825                 830
Tyr Ser Val Ser Thr Ile Glu Pro Arg Glu Asp Leu Leu Ser Pro Val
            835                 840                 845
Gln Asp Ala Asp Arg Phe Tyr Arg Gly Ile Leu Glu Pro Asp Lys His
        850                 855                 860
Cys Ser Thr Thr Pro Ala Gly Asn Ser Leu Pro Glu Tyr Pro Lys Phe
865                 870                 875                 880
Pro Cys Ser Pro Ala Ala Tyr Thr Phe Ser Pro Asn Tyr Asp Leu Arg
                885                 890                 895
Arg Pro His Gln Tyr Leu His Pro Gly Ala Gly Asp Ser Arg Leu Arg
            900                 905                 910
Glu Pro Val Leu Tyr Ser Pro Pro Ser Ala Val Phe Val Glu Pro Asn
            915                 920                 925
Arg Asn Glu Tyr Leu Glu Leu Lys Ala Lys Leu Asn Val Glu Pro Asp
        930                 935                 940
Tyr Leu Glu Val Leu Glu Lys Gln Thr Thr Phe Ser Gln Phe
945                 950                 955
```

<210> SEQ ID NO 6
<211> LENGTH: 4250
<212> TYPE: DNA
<213> ORGANISM: Homo sapiens

<400> SEQUENCE: 6

```
tagacgcgga gcccaaggag gtaaaatgca cacttgctgc cccccagtaa ctttggaaca      60
ggaccttcac agaaaaatgc atagctggat gctgcagact ctagcgtttg ctgtaacatc     120
tctcgtcctt tcgtgtgcag aaaccatcga ttattacggg gaaatctgtg acaatgcatg     180
tccttgtgag gaaaaggacg gcattttaac tgtgagctgt gaaaccggg ggatcatcag      240
tctctctgaa attagccctc cccgtttccc aatctaccac ctcttgttgt ccggaaacct     300
tttgaaccgt ctctatccca atgagtttgt caattacact ggggcttcaa ttttgcatct     360
aggtagcaat gttatccagg acattgagac cggggctttc catgggctac ggggtttgag     420
```

-continued

```
gagattgcat ctaaacaata ataaactgga acttctgcga gatgatacct tccttggctt      480
ggagaacctg gagtacctac aggtcgatta caactacatc agcgtcattg aacccaatgc      540
ttttgggaaa ctgcatttgt tgcaggtgct tatcctcaat gacaatcttt tgtccagttt      600
acccaacaat cttttccgtt ttgtgccctt aacgcacttg gacctccggg ggaaccggct      660
gaaacttctg ccctacgtgg ggctcttgca gcacatggat aaagttgtgg agctacagct      720
ggaggaaaac ccttggaatt gttcttgtga gctgatctct ctaaaggatt ggttggacag      780
catctcctat tcagccctgg tggggatgt agtttgtgag acccccttcc gcttacacgg       840
aagggacttg gacgaggtat ccaagcagga actttgccca aggagactta tttctgacta      900
cgagatgagg ccgcagacgc ctttgagcac acgggtat ttacacacca ccccggcgtc        960
agtgaattct gtggccactt cttcctctgc tgtttacaaa ccccctttga agcccctaa      1020 ggggactcgc caacccaaca agcccagggt gcgccccacc tctcggcagc cctctaagga    1080
cttgggctac agcaactatg gccccagcat cgcctatcag accaaatccc cggtgccttt    1140
ggagtgtccc accgcgtgct cttgcaacct gcagatctct gatctgggcc tcaacgtaaa    1200
ctgccaggag cgaaagatcg agagcatcgc tgaactgcag cccaagccct acaatcccaa    1260
gaaaatgtat ctgacagaga actacatcgc tgtcgtgcgc aggacagact tcctggaggc    1320
cacggggctg gacctcctgc acctggggaa taaccgcatc tcgatgatcc aggaccgcgc    1380
tttcggggat ctcaccaacc tgaggcgcct ctacctgaat ggcaacagga tcgagaggct    1440
gagcccggag ttattctatg gcctgcagag cctgcagtat ctcttcctcc agtacaatct    1500
catccgcgag attcagtctg gaacttttga cccggtccca aacctccagc tgctattctt    1560
gaataacaac ctcctgcagg ccatgccctc aggcgtcttc tctggcttga ccctcctcag    1620
gctaaacctg aggagtaacc acttcacctc cttgccagtg agtggagttt tggaccagct    1680
gaagtcactc atccaaatcg acctgcatga caatccttgg gattgtacct gtgacattgt    1740
gggcatgaag ctgtgggtgg agcagctcaa agtgggcgtc ctagtggacg aggtgatctg    1800
taaggcgccc aaaaaattcg ctgagaccga catgcgctcc attaagtcgg agctgctgtg    1860
ccctgactat tcagatgtag tagtttccac gcccacaccc tcctctatcc aggtccctgc    1920
gaggaccagc gccgtgactc ctgcggtccg gttgaatagc accggggccc ccgcgagctt    1980
gggcgcaggc ggagggggcgt cgtcggtgcc cttgtctgtg ttaattctca gcctcctgct    2040
ggttttcatc atgtccgtct tcgtggccgc cgggctcttc gtgctggtca tgaagcgcag    2100
gaagaagaac cagagcgacc acaccagcac caacaactcc gacgtgagct cctttaacat    2160
gcagtacagc gtgtacggcg gcggcggcgg cacggcggcg cacccacacg cgcacgtgca    2220
tcaccgcggg cccgcgctgc ccaaggtgaa gacgcccgcg gccacgtgt atgaatacat     2280 ccccaccca ctgggccaca tgtgcaaaaa cccccatctac cgctcccgag agggcaactc    2340
cgtagaggat tacaaagacc tgcacgagct caaggtcacc tacagcagca accaccacct    2400
gcagcagcag cagcagccgc cgccgccacc gcagcagcca cagcagcagc cccgccgca     2460 gctgcagctg cagcctgggg aggaggagag gcgggaaagc caccacttgc ggagccccgc    2520
ctacagcgtc agcaccatcg agcccggga ggacctgctg tcgccggtgc aggacgccga    2580
ccgcttttac agggcatt tagaaccaga caaacactgc tccaccaccc ccgccggcaa      2640
tagcctcccg gaatatccca aattcccgtg cagccccgct gcttacactt tctcccccaa    2700
ctatgacctg agacgcccc atcagtattt gcaccgggga gcagggaca gcaggctacg     2760 ggaaccggtg ctctacagcc ccccgagtgc tgtctttgta gaacccaacc ggaacgaata    2820
```

```
tctggagtta aaagcaaaac taaacgttga gccggactac ctcgaagtgc tggaaaaaca    2880
gaccacgttt agccagttct aaaagcaaag aaactctctt ggagcttttg catttaaaac    2940
aaacaagcaa gcagacacac acagtgaaca catttgatta attgtgttgt ttcaacgttt    3000
agggtgaagt gccttggcac gggatttctc agcttcggtg gaagatacga aaagggtgtg    3060
caatttcctt taaaatttac acgtgggaaa catttgtgta aactgggcac atcactttct    3120
cttcttgcgt gtggggcagg tgtggagaag ggctttaagg aggccaattt gctgcgcggg    3180
tgacctgtga aaggtcacag tcatttttgt agtggttgga agtgctaaga atggtggatg    3240
atggcagagc atagattcta ctcttcctct tttgcttcct cccctcccc cgccctgcc      3300 ccacctctct ttctcccctt ttaagccatg ggtgggtcta actggctttt gtggagaaat    3360
tagcacaccc aactttaat aggaaatttg ttctcttttt ccgcccctct ccttctctcc     3420
tcccctcccc tcccttctca ttccttttct ttgtttttaa aggatgtgtt tgtatgcatt    3480
ctggacattt gaattaaaaa aaaagtattg tgatcctgta aaggatcacc atagatgtgg    3540
acaaatcatt aaaattacag agctatatga tccataattg attagtcaaa ataacttatt    3600
gatgaaatat acaaatattt tattgtagca cctattttta tatgcacatt tagcattcct    3660
ctttccttca ctatttagcc tatgattttg cagaggtgtc acactgtatt aggatctgca    3720
tttctaaaac tgacgtggta tcaggaaggc attttcaatc attcaaaatg tggagaattt    3780
aatggctaaa tctttaaaag ccaatgcaac ccacccaatt gaatctgcat tttcttttaa    3840
gaaaacagag ctgattgtat cccaatgtat tttaaaaaat agggcaattg attgggccat    3900
tccgagagaa ttgttttgcaa gttttgggtt ttattagaaa atatttgaaa gtatttttat   3960
taatgaacca aaatgacatg ttcatttgac tactattgta gccgattttc gattgtttaa    4020
ccaaacccag ttgcatttgt acagatccac gtgtactggc acctcagaag accaaatcat    4080
ggactgtaca agtctctata caatgtcttt atccctgtgg gcagcaagca atgatgataa    4140
tgacaaacag gatatctgta agatggggct actgttgtta cagtctcata tgtatcccag    4200
cacatgtaat tttttaaata gtttctgaat aaacacttga taactatgtc                4250
```